United States Patent
Crum

(10) Patent No.: US 9,229,014 B2
(45) Date of Patent: Jan. 5, 2016

(54) METHODS OF ASSESSING THE NEED FOR AND THE EFFECTIVENESS OF THERAPY WITH ANTIOXIDANTS

(76) Inventor: Albert Crum, Brooklyn Heights, NY (US)

( * ) Notice: Subject to any disclaimer, the term of this patent is extended or adjusted under 35 U.S.C. 154(b) by 2057 days.

(21) Appl. No.: 11/891,323

(22) Filed: Aug. 9, 2007

(65) Prior Publication Data

US 2008/0213905 A1    Sep. 4, 2008

Related U.S. Application Data

(63) Continuation of application No. 10/797,813, filed on Mar. 10, 2004, now abandoned.

(51) Int. Cl.
*G01N 33/92* (2006.01)
*G01N 33/68* (2006.01)

(52) U.S. Cl.
CPC ............ *G01N 33/92* (2013.01); *G01N 33/6806* (2013.01); *G01N 33/6815* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,596,775 A | 6/1986 | Kimura et al. | |
| 4,859,613 A | 8/1989 | Lawrence | |
| 5,292,773 A | 3/1994 | Hirsch et al. | |
| 5,635,156 A | 6/1997 | Ildstad | |
| 5,891,622 A | 4/1999 | Morrow et al. | |
| 5,977,073 A | 11/1999 | Khaled | |
| 6,204,248 B1 | 3/2001 | Demopoulos et al. | |
| 6,284,219 B1 | 9/2001 | Ajami | |
| 6,569,683 B1 | 5/2003 | Ochi et al. | |
| 6,667,063 B2 | 12/2003 | Crum | |
| 6,709,835 B2 | 3/2004 | Crawford | |
| 6,933,120 B2 | 8/2005 | Seidman | |
| 2001/0050150 A1 | 12/2001 | Gu | |
| 2002/0034760 A1* | 3/2002 | Kindness et al. | 435/6 |
| 2002/0176900 A1 | 11/2002 | Yegorova | |

FOREIGN PATENT DOCUMENTS

| | | | |
|---|---|---|---|
| WO | 99/64022 | 12/1999 | |
| WO | 01/10231 | 2/2001 | |
| WO | 01/89518 | 11/2001 | |
| WO | WO 01/89518 | * 11/2001 | ........... A61K 31/355 |

OTHER PUBLICATIONS

Silva, A.R., et al. "L-Pyroglutamic Acid Inhibits Energy Production and Lipid Synthesis in Cerebral Cortex of Young Rats In Vitro." *Neurochemical Research* (2001) vol. 26, No. 12, pp. 1277-1283.

* cited by examiner

*Primary Examiner* — Bao Thuy L Nguyen
*Assistant Examiner* — R. Moerschell
(74) *Attorney, Agent, or Firm* — Sagun KC

(57) ABSTRACT

The invention relates to diagnostic methods for assessing the need of a subject for treatment with an anti-oxidant, or alternatively, for determining the utilization efficiency and ultimate effectiveness of anti-oxidant therapy in subjects having been treated with antioxidants. More specifically, the methods of the present invention are particularly useful in prophylactic assessment of individuals at risk for developing diseases or conditions in which oxidative stress plays a role, such that an appropriate therapeutic regimen can be prescribed for that individual, thus leading to alternative therapies and/or life style changes. The invention further relates to methods for assessing the need for, the utilization efficiency and the effectiveness of therapy in subjects having received therapy with specific antioxidant and immune enhancing formulations. Kits are also provided for measuring the levels of markers of oxidative stress and immune cell numbers.

3 Claims, No Drawings

METHODS OF ASSESSING THE NEED FOR AND THE EFFECTIVENESS OF THERAPY WITH ANTIOXIDANTS

This application is a continuation of copending application Ser. No. 10/797,813 filed Mar. 10, 2004 now abandoned claims the benefit thereof and incorporates the same by reference.

FIELD OF THE INVENTION

The invention relates to diagnostic methods for assessing the need of a subject for treatment with an anti-oxidant, or alternatively, for determining the effectiveness of anti-oxidant therapy in subjects having been treated with antioxidants. More specifically, it relates to methods for assessing the need for, or effectiveness of therapy in subjects having received therapy with, specific antioxidant and immune enhancing formulations.

BACKGROUND OF THE INVENTION

It is generally recognized that many disease processes are attributed to the presence of elevated levels of free radicals and reactive oxygen species (ROS) and reactive nitrogen species (RNS), such as superoxide, hydrogen peroxide, singlet oxygen, peroxynitrite, hydroxyl radicals, hypochlorous acid (and other hypohalous acids) and nitric oxide.

In the eye, cataract, macular degeneration and degenerative retinal damage are attributed to ROS. Among other organs and their ROS-related diseases include: lung cancer induced by tobacco combustion products and asbestos; accelerated aging and its manifestations, including skin damage and scleroderma; atherosclerosis; ischemia and reperfusion injury; diseases of the nervous system such as Parkinson disease, Alzheimer disease, muscular dystrophy, multiple sclerosis; lung diseases including emphysema and bronchopulmonary dysphasia; iron overload diseases such as hemochromatosis and thalassemia; pancreatitis; diabetes; renal diseases including autoimmune nephrotic syndrome and heavy metal-induced nephrotoxicity; and radiation injuries. Diseases of aging and chronic emotional stress also appear to be associated with a drop in glutathione levels, which allows ROS to remain active.

Certain anti-neoplastic drugs such as adriamycin and bleomycin induce severe oxidative damage, especially to the heart, limiting the patient's exposure to the drug. Redox-active metals such as iron induce oxidative damage to tissues; industrial chemicals and ethanol, by exposure and consumption, induce an array of oxidative damage-related injuries, such as cardiomyopathy and liver damage. Airborne industrial and petrochemical-based pollutants, such as ozone, nitric oxide, radioactive particulates, and halogenated hydrocarbons, induce oxidative damage to the lungs, gastrointestinal tract, and other organs. Radiation poisoning from industrial sources, including leaks from nuclear reactors and exposure to nuclear weapons, are other sources of radiation and radical damage. Other routes of exposure may occur from living or working in proximity to sources of electromagnetic radiation, such as electric power plants and high-voltage power lines, x-ray machines, particle accelerators, radar antennas, radio antennas, and the like, as well as using electronic products and gadgets which emit electromagnetic radiation such as cellular telephones, and television and computer monitors.

Mammalian cells have numerous mechanisms to eliminate these damaging free radicals and reactive species. One such mechanism includes the glutathione system, which plays a major role in direct, destruction of reactive oxygen compounds.

Perhaps one of the most important contributions of glutathione to mammalian health is its participation in the proper functioning of the immune system to respond to infection or other types of trauma. It is known that weakening of the immune system caused by infection or other traumas occurs concurrently with depletion of glutathione in body tissues. It is known, also, that such weakening can be reversed by replenishing the body's level of glutathione by intracellular synthesis. It is believed that glutathione accomplishes its salutary effects by protecting immune cells against the ravages of oxidizing agents and free radicals.

Until recently, the lack of specific and dependable methods for evaluating oxidant stress in vivo made it very difficult to establish a cause and effect relationship between free radical-generating agents or conditions and disease pathology. Furthermore, the various treatment strategies with anti-oxidants have been difficult to monitor due to the lack of techniques sufficiently sensitive to reliably provide an index of oxidative damage in vivo.

For example, there is currently substantial evidence that oxidation of LDL occurs in vivo, and results of animal studies suggest that this may lead to the formation and build up of atherosclerotic plaques. Although epidemiological data support a role for antioxidants in the prevention of clinical events, intervention trials thus far have given mixed results (Steinberg D, Witztum J L. Lipoproteins, lipoprotein oxidation, and atherogenesis. In Chien K R, ed. *Molecular Basis of Cardiovascular Disease.* Philadelphia, Pa.: W.B. Saunders Co., 1998:458-475). This may be due, in part, to the fact that until now techniques to adequately provide an index of in vivo lipid peroxidation have not been available, which could be used to design and monitor effective antioxidant intervention trials to adequately test the oxidation hypothesis.

Furthermore, there are no set measures to identify high-risk groups that would theoretically benefit most from antioxidant therapies or interventions. Additionally, there are no reliable means to measure or determine the effectiveness of such interventions in vivo. In the absence of such methodology, current (and future) clinical trials testing natural (or synthetic) antioxidants, which utilize clinical endpoints, may give incorrect conclusions regarding the role of antioxidants in specific disease states. This is a possibility because of the inclusion of populations that would not be expected to benefit from antioxidant supplementation, and/or because the dose or agent yielded insufficient antioxidant protection.

It is with respect to the development of more sensitive and accurate assays for assessing the need for intervention with anti-oxidant therapy and for monitoring the effectiveness and utilization efficiency of novel anti-oxidants that the current invention is directed.

SUMMARY OF THE INVENTION

In its broadest aspect, the present invention relates to methods for assessing the need of a subject for treatment with an antioxidant, or alternatively, if a subject is currently being treated with an anti-oxidant, the invention provides for measuring the utilization efficiency of the anti-oxidant and the subsequent effectiveness of therapy with the anti-oxidant. It is also an object of the present invention to provide a means for determining the anti-oxidative effective amounts of specific anti-oxidant formulations for delivery to a subject in need of such therapy. More particularly, the invention provides for methods for determining the amount of anti-oxidants necessary to increase glutathione synthesis or re-synthesis in a patient in need of such therapy.

Accordingly, a first aspect of the invention provides for a method for assessing the need for treatment with an anti-oxidant comprising the steps of:
a) collecting a sample of body fluid from a subject suspected of needing such treatment;
b) measuring the amount of lipid peroxide and pyroglutamic acid (PGA) levels in said sample;
c) measuring the level of blood plasma glutathione;
d) comparing the amount of lipid peroxide and pyroglutamic acid in said sample with that of a normal standard; and
e) comparing the level of blood plasma glutathione with that of a normal standard; and
wherein the presence of lipid peroxide and pyroglutamic acid in said sample and the blood plasma levels of glutathione are present in amounts that lie outside the normal range are indicative of a need for anti-oxidant treatment.

In a particular embodiment, the patient or subject is preferably an animal, including but not limited to animals such as monkeys, cows, pigs, horses, chickens, cats, dogs, etc., and is preferably a mammal, and most preferably human. In one embodiment, a non-human mammal is the subject. In another embodiment, a human mammal is the subject. In yet another particular embodiment, the subject in need of treatment with an anti-oxidant also experiences a reduction in immune cell number and/or function. In another particular embodiment, the immune cell is selected from the group consisting of a T cell, a B cell or a natural killer cell. In yet another particular embodiment, the T cell is selected from the group consisting of a CD4+ or a CD8+ T cell.

In another particular embodiment, the sample of body fluid is urine. In another particular embodiment, the sample of body fluid is whole blood. In a yet further particular embodiment, the sample of body fluid is plasma or serum.

In another particular embodiment, the anti-oxidant is selected from the group consisting of glutathione precursors, IMMUNE FORMULATION 100™ and IMMUNE FORMULATION 200™.

A second aspect of the invention provides a method for measuring the effectiveness of therapy with an anti-oxidant in a subject comprising the steps of:
a) collecting a sample of body fluid from a subject being treated with an anti-oxidant;
b) measuring the amount of lipid peroxide and pyroglutamic acid in said sample;
c) measuring the level of blood plasma glutathione;
d) comparing the amount of lipid peroxide and pyroglutamic acid in said sample with that of a normal standard;
e) comparing the level of blood plasma glutathione with that of a normal standard; and
wherein the presence of normal levels of lipid peroxide and pyroglutamic acid in said sample and the presence of normal levels of blood plasma glutathione are an indication of effectiveness of the anti-oxidant therapy.

In a particular embodiment, the method may further comprise determining whether immune cell number and/or function is normalized in the subject, wherein the normalization is indicative of the effectiveness of therapy with the anti-oxidant. In another particular embodiment, the immune cell is selected from the group consisting of a T cell, a B cell or a natural killer cell. The method of claim 9, wherein said T cell is selected from the group consisting of a CD4+ T cell or a CD8+ T cell. In another particular embodiment, The method of claim 7, wherein said anti-oxidant is selected from the group consisting of glutathione precursors, IMMUNE FORMULATION 100™ or IMMUNE FORMULATION 200™. In yet another particular embodiment, the sample of body fluid is urine. In another particular embodiment, the sample of body fluid is whole blood. In a yet further particular embodiment, the sample of body fluid is plasma or serum.

In another particular embodiment, the anti-oxidant is selected from the group consisting of glutathione precursors, IMMUNE FORMULATION 100™ or IMMUNE FORMULATION 200™.

In yet another preferred embodiment, the method further comprises measurement of a secondary endpoint for monitoring the effectiveness of therapy. For example, wherein the patient under treatment with the anti-oxidant therapy is suffering from a disease which is, in part, caused by high levels of oxidant stress, or where a particular drug treatment itself results in oxidative damage to a particular tissue or organ, such as with chemotherapy, it is beneficial to measure the effectiveness of therapy with the anti-oxidant using the steps described above. However, in diseases such as atherosclerosis or cardiovascular disease, whereby oxidized low density lipoprotein (LDL) has been implicated in the initiation and/or exacerbation of the disease process, it would be beneficial to monitor the effects of the antioxidant therapy not only on lipid peroxide, PGA and glutathione levels, but also on for example, cardiac function to determine whether the antioxidant therapy has effects on the sequelae of high oxidative stress levels, such as cardiovascular disease or atherosclerosis. The secondary endpoint may include lowering of triglycerides, LDLs or increasing of high density lipoproteins (HDLs), or measurement of cardiac function using standard testing known to one skilled in the art.

A third aspect of the invention provides a method for measuring the utilization efficiency of an anti-oxidant comprising the steps of:
a) collecting samples of body fluid from a subject being treated with an anti-oxidant each day after initiation of therapy and up to 14 days after therapy has been initiated;
b) measuring the amount of lipid peroxide and pyroglutamic acid in said samples;
c) measuring the level of blood plasma glutathione;
d) comparing the amount of lipid peroxide and pyroglutamic acid in said samples with that of a normal standard;
e) comparing the level of blood plasma glutathione with that of a normal standard; and
wherein the presence of normal levels of lipid peroxide and pyroglutamic acid in said samples and the presence of normal levels of blood plasma glutathione are an indication of efficiency of utilization of the anti-oxidant.

In a particular embodiment, the method further comprises determining whether immune cell number and/or function is normalized in the subject, wherein the normalization is indicative of the utilization efficiency of the anti-oxidant. In another particular embodiment, the immune cell is selected from the group consisting of a T cell, a B cell or a natural killer cell. In another particular embodiment the T cell is selected from the group consisting of a CD4+ or a CD8+ T cell. In yet another particular embodiment, the sample of body fluid is urine. In another particular embodiment, the sample of body fluid is whole blood. In a yet further particular embodiment, the sample of body fluid is plasma or serum.

In another particular embodiment the anti-oxidant is selected from the group consisting of glutathione precursors, IMMUNE FORMULATION 100™ or IMMUNE FORMULATION 200™.

In another preferred embodiment, if the levels of lipid peroxides, pyroglutamic acid, and glutathione are not normalized, the levels of antioxidants are increased in dosage until such normalization occurs.

A fourth aspect of the invention provides a method for determining the amount of IMMUNE FORMULATION 100™ or IMMUNE FORMULATION 200™ that is necessary to increase glutathione synthesis or re-synthesis in a subject in need of such therapy, comprising the steps of:
  a) collecting a series of body fluid samples from a subject suspected of being in need of such treatment, wherein said body fluid samples are collected prior to the start of treatment, and daily after the start of treatment for about 14 days;
  b) measuring the amount of lipid peroxide and pyroglutamic acid in said body fluid samples;
  c) comparing the amount of lipid peroxide and pyroglutamic acid in said body fluid samples with that of normal standards;
  d) measuring the amount of glutathione increase in blood samples;
  e) comparing the amount of glutathione in said blood samples with that of normal standards; and
  wherein the normalization of lipid peroxide and pyroglutamic acid levels in said body fluid samples correlates with the synthesis or re-synthesis of glutathione in the patients receiving IMMUNE FORMULATION 100™ or IMMUNE FORMULATION 200™.

In a particular embodiment, the sample of body fluid is urine. In another particular embodiment, the sample of body fluid is whole blood. In a yet further particular embodiment, the sample of body fluid is plasma or serum.

In another preferred embodiment, if the levels of lipid peroxides, pyroglutamic acid, and glutathione are not normalized, the levels of IMMUNE FORMULATION 100™ or IMMUNE FORMULATION 200™ are increased in dosage and the methods described above are repeated until such normalization occurs.

A fifth aspect of the invention provides a method for determining the amount of IMMUNE FORMULATION 100™ or IMMUNE FORMULATION 200™ that is necessary to reduce urine pyroglutamic acid in a subject in need of such therapy, comprising the steps of:
  a) collecting a series of urine samples from a subject suspected of being in need of such treatment, wherein said samples are collected prior to the start of treatment, and daily after the start of treatment for about 14 days;
  b) measuring the amount of pyroglutamic acid in said samples;
  c) comparing the amount of pyroglutamic acid in said samples with that of a normal standard; and
wherein the reduction of pyroglutamic acid to normal levels in said samples correlates with the amount of IMMUNE FORMULATION 100™ or IMMUNE FORMULATION 200™ sufficient to achieve a beneficial effect.

In a preferred embodiment, if the levels of urine pyroglutamic acid are not normalized, the levels of IMMUNE FORMULATION 100™ or IMMUNE FORMULATION 200™ are increased in dosage until such normalization occurs, and the methods described above are repeated until such time when normalization is achieved.

A sixth aspect of the invention provides a method for determining the amount of IMMUNE FORMULATION 100™ or IMMUNE FORMULATION 200™ that is necessary to reduce urine lipid peroxide in a subject in need of such therapy, comprising the steps of:
  a) collecting a series of urine samples from a subject suspected of being in need of such treatment, wherein said samples are collected prior to the start of treatment, and daily after the start of treatment for about 14 days;
  b) measuring the amount of lipid peroxide in said samples;
  c) comparing the amount of lipid peroxide in said samples with that of a normal standard; and
wherein the reduction of lipid peroxide to normal levels in said samples correlates with the amount of IMMUNE FORMULATION 100™ or IMMUNE FORMULATION 200™ sufficient to achieve a beneficial effect.

In a preferred embodiment, if the levels of urine lipid peroxide are not normalized, the levels of IMMUNE FORMULATION 100™ or IMMUNE FORMULATION 200™ are increased in dosage until such normalization occurs, and the methods described above are repeated until such time when normalization is achieved.

A seventh aspect of the invention provides a method for determining an orally anti-oxidative effective amount of IMMUNE FORMULATION 100™ or IMMUNE FORMULATION 200™ sufficient to diminish urine lipid peroxide and pyroglutamic acid levels and concurrently increase blood plasma glutathione levels, comprising the steps of:
  a) collecting blood plasma and urine samples prior to administration of IMMUNE FORMULATION 100™ or IMMUNE FORMULATION 200™ and daily after the start of administration for about 14 days;
  b) measuring urine levels of lipid peroxide and pyroglutamic acid;
  c) measuring blood plasma glutathione levels;
  d) determining whether a decrease in lipid peroxide and pyroglutamic acid levels correlates with an increase in glutathione levels; and
wherein said correlation establishes an orally anti-oxidative effective amount of IMMUNE FORMULATION 100™ or IMMUNE FORMULATION 200™.

In a preferred embodiment, the levels of lipid peroxide, pyroglutamic acid and glutathione are measured concurrently. In a further preferred embodiment, if the levels of lipid peroxides, pyroglutamic acid, and glutathione are not normalized when first tested, the levels of IMMUNE FORMULATION 100™ or IMMUNE FORMULATION 200™ are increased in dosage and the methods described above are repeated until such normalization occurs.

An eighth aspect of the invention provides for establishing the interdependence of lipid peroxides, pyroglutamic acid, glutathione, and immune cell number and/or function in a subject suffering from oxidative stress, comprising the steps of:
  a) collecting a urine sample from a subject suspected of being under oxidative stress;
  b) assaying the urine for the presence of lipid peroxides and pyroglutamic acid;
  c) collecting a sample of whole blood;
  d) separating the cellular components from the liquid portion of whole blood;
  e) measuring glutathione in the liquid portion of whole blood obtained in step d);
  f) measuring the number of CD4+ T cells and CD8+ T cells in the cellular component of whole blood from step d); and
  g) measuring the natural killer cell activity from the cellular component of whole blood obtained from step d);
wherein a finding of decreased plasma glutathione levels, an increase in urinary lipid peroxides and pyroglutamic acid, and a decrease in the number of CD4+ and CD8+ T cells and natural killer cell activity provides support for the interdependence of the level of oxidative stress in said subject and immune cell number and/or function.

A ninth aspect of the invention provides for a method for determining an immune enhancing effective amount of IMMUNE FORMULATION 100™ or IMMUNE FORMULATION 200™ sufficient to normalize CD4+, CD8+ T cell numbers and natural killer cell activity in a subject suspected of experiencing oxidative stress, comprising the steps of:
 a) collecting whole blood samples prior to administration of IMMUNE FORMULATION 100™ or IMMUNE FORMULATION 200™ and daily after the start of administration for about 14 days;
 b) separating the cellular component of the whole blood from the liquid component; and
 c) measuring the number of CD4+ and CD8+ T cells and natural killer cell activity using the cellular component from step b);
wherein a correlation between the dose of IMMUNE FORMULATION 100™ and IMMUNE FORMULATION 200™ that is sufficient to normalize CD4+, CD8+ T cell numbers and natural killer cell activity establishes an immune enhancing effective amount of IMMUNE FORMULATION 100™ or IMMUNE FORMULATION 200™.

A tenth aspect of the invention provides for a method for determining an orally anti-oxidative effective amount and an immune enhancing effective amount of IMMUNE FORMULATION 100™ or IMMUNE FORMULATION 200™ sufficient to normalize lipid peroxides, pyroglutamic acid and glutathione levels in a subject suspected of experiencing oxidative stress, wherein said normalization of lipid peroxides, pyroglutamic acid and glutathione levels results in immune enhancement, comprising the steps of:
 a) collecting whole blood and urine samples prior to administration of IMMUNE FORMULATION 100™ or IMMUNE FORMULATION 200™ and daily after the start of administration for about 14 days;
 b) measuring urine levels of lipid peroxide and pyroglutamic acid;
 c) separating the cellular component of the whole blood from the liquid component;
 d) measuring blood plasma glutathione levels using the liquid component from step c);
 e) measuring the number of CD4+ and CD8+ T cells and natural killer cell activity using the cellular component from step c);
 f) determining whether a decrease in urinary lipid peroxide and pyroglutamic acid levels correlates with an increase in glutathione levels, and whether the normalization of the levels of all three of these products relates to a normalization of CD4+ and CD8+ T cell numbers and normalization of natural killer cell activity; and
wherein said correlation establishes an orally anti-oxidative effective amount and an immune enhancing effective amount of IMMUNE FORMULATION 100™ or IMMUNE FORMULATION 200™.

In a particular embodiment, said correlation further establishes the interrelationship of lipid peroxides, pyroglutamic acid, glutathione and immune functions and the level of oxidative stress in said subject that results in depressed immune functions.

An eleventh aspect of the invention provides kits for measuring oxidative stress in an individual suspected of suffering from oxidative stress. Such a kit may contain all of the reagents necessary to measure at least three markers of oxidative stress at the same time. The assay kit may be formatted for use as a competitive or non-competitive ELISA assay. Alternatively, the kit may be structured in much the same way as a take home pregnancy kit, for example, using a test strip format. The kit may also contain binding partners, for example, antibodies specific for certain immune cells, such as CD4+ T cells, CD8+ T cells and natural killer cells. Thus, the kits of the present invention may be capable of monitoring both oxidative stress and immune cell number.

In a particular embodiment, the kit for measuring oxidative stress in a subject comprises:
 a) a solid substrate containing immobilized binding partners specific for at least three markers for oxidative stress;
 b) either:
  i) an enzyme conjugated second binding partner to the oxidative stress markers; or
  ii) a biotinylated second binding partner to the oxidative stress markers;
 c) either:
  i) the enzyme substrate and the developing reagents specific for the enzyme conjugated second binding partner from step b) i); or
  ii) a streptavidin conjugated third binding partner specific for the second binding partner of step b) ii);
 d) buffers for washing and sample dilution;
 e) standards for each of the at least three markers of oxidative stress; and
 f) instructions for use of said kit.

In another particular embodiment, the binding partner is an antibody. In another particular embodiment the kit further comprises additional compartments to which have been attached antibodies specific for cell surface markers for CD4+ T cells, CD8+ T cells and natural killer cells. In a preferred embodiment, the markers of oxidative stress are selected from the group consisting of lipid peroxide, pyroglutamic acid and glutathione. In another preferred embodiment, the antibody is selected from a monoclonal antibody, a polyclonal antibody, a chimeric antibody, and any combination thereof.

A twelfth aspect of the invention provides a method for providing a course of therapy for an individual suspected or known to be suffering from oxidative stress comprising
 a) determining the identity and level of at least three markers of oxidative stress in a sample of body fluid from said individual, said markers being indicative of the extent of oxidative stress; and
 b) selecting the appropriate course of therapy for said individual suffering from oxidative stress and the sequelae thereof.

In a particular embodiment, the method includes administering said appropriate course of therapy to said individual. In another particular embodiment, the method provides a course of therapy for an individual suspected or known to be suffering from oxidative stress and monitoring the success of said therapy comprising:
 a) determining the identity and level of at least three markers of oxidative stress in a sample of body fluid from said individual, said marker being indicative of the extent of oxidative stress;
 b) selecting the appropriate course of therapy for said individual suffering from said oxidative stress;
 c) administering said appropriate course of therapy to said individual; and monitoring the success of said therapy by measuring a normalization in levels of said markers of oxidative stress.

In a preferred embodiment, the method provides for said course of therapy comprising administering IMMUNE FORMULATION 100™ or IMMUNE FORMULATION 200™ to said individual.

Other advantages of the present invention will become apparent from the ensuing detailed description.

DETAILED DESCRIPTION INVENTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the particular methods and materials are now described. All publications mentioned herein are incorporated herein by reference.

DEFINITIONS

The terms used herein have the meanings recognized and known to those of skill in the art; however, for convenience and completeness, particular terms and their meanings are set forth below.

"Treatment" refers to the administration of an antioxidant or the performance of procedures with respect to a subject, for either prophylaxis (prevention) or to cure the infirmity or malady in the instance where the subject is afflicted.

As used herein, "assessing the need for treatment" refers to determining whether a subject would be a candidate for therapy with an anti-oxidant. The determination would be made based on the particular disease and symptoms associated with the disease, and whether or not the cause of the disease or condition can be attributed, at least in part, to high levels of oxidation of cells, tissues, proteins or other molecular or chemical entities which are candidates for damage caused by oxidative stress, as evidenced by high levels of lipid peroxide and high levels of PGA in the urine and low levels of glutathione in the blood.

A "therapeutically effective amount" is an amount sufficient to decrease or prevent the symptoms associated with the disease caused by or attributed to oxidative stress.

By "patient" or "subject" is meant a human or non-human mammal that may benefit from the therapies described in the present application, for example, anti-oxidant therapy. The anti-oxidants may be administered to subjects already having a disease or condition whose symptoms and sequelae are attributed to oxidation of proteins, cells or tissues, or particular molecular entities or chemical compounds, and whose symptoms or sequelae may be alleviated by anti-oxidant therapy. Alternatively, the subjects may be predisposed to diseases or conditions caused by high levels of oxidation, for which therapy with an anti-oxidant may be beneficial. Accordingly, the subject may be treated prophylactically with the anti-oxidant therapy. Diseases or conditions for which such anti-oxidant therapy would be beneficial may be selected from the group consisting of autoimmune or degenerative diseases including acetaminophen poisoning, ADD, Addison's disease, aging, AIDS, alopecia greata, ALS, Alzheimer's disease, anemia (hemolytic), ankylosing spondylitis, arteriosclerosis, arthritis (including osteoarthritis and rheumatoid arthritis), asthma, autism, autoimmune disease, Behcet's disease, burns, cachexia, cancer, candida infection, cardiomyopathy (idiopathic), chronic fatigue syndrome, colitis, coronary artery disease, cystic fibrosis, diabetes, Crohn's disease, eczema, emphysema, Epstein Barr Viral (EBV) syndrome, fibromyalgia, free radical overload, Goodpasture syndrome, Grave's disease, hepatic dysfunction (liver disease), hepatitis B, hepatitis C, HIV or patients suffering from AIDS, hypercholesteremia (high blood cholesterol), herpes, infections (viral, bacterial and fungal), inflammatory bowel disease (IBD), lupus, macular degeneration, malnutrition, Meniere's disease, multiple sclerosis, myasthenia gravis, neurodegenerative diseases, nutritional disorers, Parkinson's disease, Pemphigus vulgaris, Primary Billiary Cirrhosis, progeria, psoriasis, rheumatic fever, sarcoidosis, scleroderma, shingles, stroke, surgery, toxic poisoning, trauma, vasculitis, vitiligo, and Wegener's granulomatosis (nutritionadvisor.com/immunocalFAQ.html).

The term "utilization efficiency" as used herein refers to how well the body uses the anti-oxidants which are administered to counteract the damage caused by free radicals or other oxidizing agents which play a role in the damage to cells and tissues. The efficiency of use may be determined by either a direct measurement of the oxidized material, for example, the levels of lipid peroxide and the levels of PGA in the urine or a specific oxidized protein such as oxidized low density lipoprotein (LDL), associated with cells or tissues, or found circulating in the bloodstream. The "utilization efficiency" is considered to be more effective when the level of oxidized material is decreased after therapy with an anti-oxidant compared to its level prior to the start of therapy with an antioxidant.

By "effectiveness of therapy" is meant that upon treating a subject with an anti-oxidant, one can determine whether the treatment has resulted in the desired outcome. For example, in the case of treating a patient having high levels of an oxidized protein, for example, such as oxidized LDL (low density lipoprotein), with an anti-oxidant, one may observe a decrease not only in the amount of oxidized LDL, but also in the sequelae associated with oxidized LDL, such as a decrease in the amount of atherosclerotic plaque which ultimately may lead to an increase or risk of heart failure. In addition, patients suffering from HIV may also have sequelae that can be monitored after treatment with an antioxidant. These may include, for example, changes in the number of CD4+ T cells and CD8+ T cells and their corresponding ratios.

"IMMUNE FORMULATION 100™" refers to a non-toxic nutritional composition useful for increasing glutathione production in a mammal in order to enhance the immune activity of the mammal. This composition contains the following as essential active ingredients:
  a: a catalytic quantity of elemental selenium or a water soluble selenium precursor;
  b: from about 5% to about 95% of a special whey product containing from about 65% to about 85% protein which is from about 65% to about 100% undenatured; and
  c: from about 5% to about 95% by weight of colostrum;
the percent by weight of each component based on the total weight of the composition. This material is further described and claimed in U.S. Pat. No. 6,667,063.

"IMMUNE FORMULATION 200™" refers to a nutritional or therapeutic composition useful for treatment of mammals to enhance immune activity. This composition contains the following as essential active ingredients: a catalytic quantity of a selenium source together with glutathione precursors which are a mixture of glutamic acid, cystine or another related cystine precursor, and glycine in a molar ratio of about 1:0.5:1, the amount of glutathione precursors being effective to increase the content of glutathione in the body tissue of the mammal above that of a pretreatment level thereby to enhance immune activity. This material is further described and claimed in U.S. Pat. No. 6,592,908.

Glutathione is a tripeptide and a major reducing agent in the mammalian body. Its chemical structure is:

or, more simply
GLU-CYS-GLY

Its chemical name is glutamyl-cysteinyl-glycine. Like many other small peptides in the mammalian body, it is not synthesized by procedures involving DNA, RNA and ribosomes. Rather, it is synthesized from the amino acids available in the body and selenium by procedures utilizing enzymes and other body components such as adenosine triphosphate as an energy source.

The term "anti-oxidative effective amount" as used herein refers to an amount of an anti-oxidant, such as for example, IMMUNE FORMULATION 100™ or IMMUNE FORMULATION 200™ which, when delivered to a patient or subject in need of such therapy results in reduction of the proteins, cellular components, or tissue components that have been oxidized and subsequently damaged or have reduced functional capacity as a result of being oxidized. An "anti-oxidative effective amount" of an anti-oxidant is the amount of the anti-oxidant needed to restore certain functional capacities to the proteins, cells or tissues that are damaged by oxidation. The anti-oxidants are dietary supplements containing nutritional products. If an excess of any amino acid is used, it will presumably be of nutritional value or may be metabolized.

"Pyroglutamic acid" or "PGA" is a keto derivative of proline that is formed nonenzymatically from glutamate, glutamine, and gamma-glutamylated peptides. It is also produced by the action of gamma-glutamylcyclotransferase. It is also referred to as 5-oxoproline, 5-pyrrolidone-2-carboxylic acid, or pyrrolidone-5-carboxylate. Elevated levels are often associated with problems of glutamine or glutathione metabolism.

"Lipid peroxides" are fats that have been damaged by excess free radical activity. Lipid peroxides are the products of the chemical damage done by oxygen free radicals to the lipid components of cell membranes. This oxidative damage, caused by free radical pathology, is thought to be a basic mechanism underlying many diverse pathological conditions—atherosclerosis, cancer, aging, rheumatic diseases, allergic inflammation, cardiac and cerebral ischemia, respiratory distress syndrome, various liver disorders, irradiation and thermal injury, and toxicity induced by certain metals, solvents, pesticides and drugs. Measurement of lipid peroxide levels plays a significant role in evaluating cellular damage caused by oxidative stress and determining an individual's specific need for antioxidant supplementation. The level of lipid peroxides is an index of cellular membrane damage caused by the action of free radicals. The organelle membranes, such as those of the mitochondria, lysosomes, peroxisomes, and DNA can be damaged as well. This damage is lipid peroxidation, resulting from an excess of prooxidants over antioxidants. Such excess, categorized as oxidative stress, can damage membrane proteins and cholesterol, as well as membrane lipids. The elevation of lipid peroxides can serve as an early warning of the long-term effects of oxidative stress. The natural sequel of oxidative stress is chronic degenerative disease. One example is that peroxidation of low density lipoproteins contributes to atherosclerosis. Other associated diseases include coronary artery disease and cancer, the leading causes of death in the United States.

The term "free radicals" refers to a chemical species that possesses an unpaired electron in the outer (valence) shell of the molecule. This is the reason they are highly reactive and thus have low chemical specificity i.e., they can react with most molecules in their vicinity. This includes proteins, lipids, carbohydrates and DNA. Free radicals attack the nearest stable molecule, thus "stealing" its electron. When the attacked molecule loses its electron, it becomes a free radical itself, thus beginning a chain reaction. It continues until the final result is the disruption of a living cell. Free radicals are produced continuously in cells either as by-products of metabolism or deliberately as in phagocytosis (Cheeseman, K. H. and Slater, T. F., Br Med. Bull. 1993 July; 49(3): 481-93).

"Surrogate biomarker" or "biomarker" or "marker" as used herein, refers to a highly specific molecule, the existence and levels of which are causally connected to a complex biological process, and reliably captures the state of said process. Furthermore, a surrogate biomarker, to be of practical importance, must be present in samples that can be obtained from individuals without endangering their physical integrity or well-being, preferentially from biological fluids such as blood, plasma, urine, saliva or tears. The biomarkers of oxidative damage, as used herein, include increased lipid peroxides and pyroglutamic acid and decreased glutathione. The levels of these biomarkers should reflect the degree of oxidative stress in the body and are the result of certain diseases or conditions and should continue to accumulate or remain stable in the body until released, excreted or neutralized. Furthermore, the presence of these biomarkers, in particular, lipid peroxides and pyroglutamic acid, should reflect the need for anti-oxidant therapy. The normalization of these biomarkers as well as normalization of the levels of glutathione should also reflect the utilization efficiency and effectiveness of anti-oxidative therapy as provided in the present application.

A person "suspected of being in need of such treatment" in terms of the methods of the present invention may refer to an individual suffering from symptoms suggestive of lowered immunity, such as frequent infections or colds.

By the term "sequelae" of oxidative stress is meant the conditions following as a consequence of the level or duration of oxidative stress. This may include a predisposition for acquiring infections, or a predisposition to certain pathological conditions or diseases. It may include cellular or tissue damage resulting from the persistence and/or buildup of free radicals in particular tissues, for example, in kidney tissue following treatment with certain drugs such as adriamycin, or following an injury to the brain or spinal cord.

The term "antibody" as used herein includes intact molecules as well as fragments thereof, such as Fab and F(ab')$_2$, which are capable of binding the epitopic determinant. Antibodies that bind the proteins or the markers of oxidative stress of the present invention can be prepared using intact polypeptides or fragments containing small peptides of interest as the immunizing antigen attached to a carrier molecule. Commonly used carriers that are chemically coupled to peptides include bovine or chicken serum albumin, thyroglobulin, and other carriers known to those skilled in the art. The coupled peptide is then used to immunize the animal (e.g., a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397.). The antibody may be a human or a humanized antibody. The antibody may be a single chain antibody. (See, e.g., Curiel et al., U.S. Pat. No. 5,910,486 and U.S. Pat. No. 6,028,059). The various portions of the chimerized antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al, U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; and Queen et al., U.S. Pat. Nos. 5,585,089, 5,698,761 and 5,698,762. See also, Newman, R. et al., Bio-Technology, 10: 1455-1460 (1992), regarding primatized antibody, and Ladner et al., U.S. Pat. No. 4,946,778 and Bird, R. E. et al., Science, 242: 423-426 (1988)) regarding single chain antibodies. The antibody may be prepared in, but not limited to, mice, rats, rabbits, goats, sheep, swine, dogs, cats, or horses.

General Description

Finding a means of protecting cells and/or molecules from the effects of free radicals is of obvious medical importance. These free radicals have been associated with a large variety of conditions in which cells die, resulting in severe clinical consequences. Furthermore, the need for protection of cells and/or molecules from the damage caused by free radicals has been addressed, in part, by administration of anti-oxidants. However, it has been difficult to measure the presence of free radicals due to their very short half-life. Furthermore, the methods that are available, such as electron spin resonance and spin trapping methods (Cheeseman, K. H. and Slater, T. F., Br Med Bull. 1993 July; 49(3): 481-93) using exogenous compounds having a high affinity for free radicals, have poor sensitivity and are not 100% accurate, that is, they produce only semi-quantitative data.

Therefore, it is necessary to find alternate strategies to assess the presence of free radicals and the level of oxidative stress in an individual patient. A commonly used technique is to measure a marker of free radicals rather than the radical itself (Slater, T. F., Methods Enzymol. 1984; 105:283-93; Pryor W. A. and Godber S. S., Free Radic Biol Med. 1991; 10(3-4):173). Thus, various assays have been devised to measure these markers of oxidative stress.

Likewise, it is difficult to assess whether an individual is in need of treatment with an anti-oxidant. Furthermore, once it has been determined that an individual would benefit from such therapy, it is important to be able to assess whether the therapy as delivered is being utilized to its full capacity. And finally, it is necessary to determine how effective that therapy is by assessing an individual's response and outcome following such therapy.

Accordingly, the present invention provides a multidimensional and comprehensive method for assessing the need for treatment of a subject with an anti-oxidant. Previous tests for measuring an individual's level of oxidative stress has relied primarily on the measurement of one or two markers of oxidative stress, such as lipid peroxides. The present invention provides for the quantitation of several markers of oxidative stress, including lipid peroxides, pyroglutamic acid, and glutathione. In addition, since it is becoming more apparent that an individual's immune status may depend in part on the level of glutathione present in vivo, the present invention provides for concurrent measurement of immune cell numbers and activity, in particular, the number of CD4+ and CD8+ T cells, and the level of natural killer cell activity. The present invention will thus provide for the interrelationship between lipid peroxides, pyroglutamic acid, and glutathione, as well as the immune functions associated with adequate levels of antioxidants, and the markers thereof. There have been no known studies of which the inventor is aware that provides this comprehensive and quantitative manner of assessment of oxidative stress and related immune functions. It is a further object of the present invention to be able to measure the utilization efficiency of the anti-oxidant therapy once an individual has started therapy with an anti-oxidant. It is yet a further object of the present invention to be able to measure the effectiveness of the anti-oxidant therapy once an individual has started and then completed the therapy with an anti-oxidant.

Furthermore, this invention is based, in part, on the use of novel IMMUNE FORMULATIONs, in particular, IMMUNE FORMULATION 100™ or IMMUNE FORMULATION 200™, and provides for methods of determining the amount of these formulations necessary to increase glutathione synthesis or re-synthesis in a patient in need of such therapy and to reduce the amounts of lipid peroxides and pyroglutamic acid levels in these patients. The ability to monitor the elevation in plasma glutathione levels while concurrently measuring a decrease in two oxyradical metabolites, urine lipid peroxide and pyroglutamic acid, provides a more quantitative and accurate assessment of a patient's level of oxidative stress, and allows for adjustment in dose and duration of appropriate anti-oxidant therapies, including those described herein.

Accordingly, the present invention provides for tracking two metabolites from their respective metabolic pathways to establish anti-oxidant need before treatment with specific anti-oxidant formulations, and after the administration of the anti-oxidants to demonstrate the utilization efficiency of the therapy and eventual effectiveness of the therapy on glutathione synthesis. In preferred embodiments, the anti-oxidant therapies are IMMUNE FORMULATION 100™ or IMMUNE FORMULATION 200™.

Thus, it is important to track the oxyradical metabolite urine lipid peroxide before and after therapy to determine where the level falls as compared to the normal range. The normal range as determined by standard clinical testing, such as that provided by Metametrix Clinical Laboratory, is about 8.9 to 13.3 nM/mg.

Furthermore, it is also crucial to track the catabolic breakdown product of glutathione, known as pyroglutamic acid (PGA) in the urine and to determine where the level falls as compared to the normal range. The normal range as determined by standard clinical testing, such as that provided by Metametrix Clinical Laboratory, is about <80 µg/mg of creatinine.

Therefore, establishing the patient's baseline level of these metabolites will help to establish whether there is a need for anti-oxidant therapy. If the level falls outside of the normal range for these metabolites, there is a need for initiation of anti-oxidant therapy.

Thus, once certain anti-oxidant deficiencies have been established which may be responsive to therapies with antioxidants, it would be imperative to determine the utilization efficiency of such therapy once it has been initiated. Therapies such as IMMUNE FORMULATION 100™ or IMMUNE FORMULATION 200™ would in all likelihood be most beneficial, due to the effects of these formulations on production of glutathione and its anti-oxidant activity per se and/or its antioxidant activity with selenium through glutathione peroxidase. Afterwards, the overall effectiveness of such therapies must be monitored such as by the methods of the present invention to determine whether normal levels of lipid peroxides, PGA and glutathione have been established. The determination as to whether there is a need for continued therapy would be made by the health care assistant, physician, or by self-assessment.

Methods of Quantifying Lipid Peroxides

When a fatty acid is peroxidized it is broken down into aldehydes, which are excreted. Aldehydes such as thiobarbituric acid reacting substances (TBARS) have been widely accepted as a general marker of free radical production, with the most commonly measured TBARS being malondialdehyde (Esterbauer, H, Jürgens, G, Quehenberger, O, & Koller, E, *J Lipid Res* 1987, 28:495-509; Buege, J A & Aust, S D, Methods Enzymol 1978, 52:302-310; Wallin, B & Camejo, G, Scand J Clin Lab Invest 1994, 54:341-346; El-Saadani, M, Esterbauer, H, El-Sayed, M, Goher, M, Nassar, A Y, & Jürgens, G A, J Lipid Res 1989, 30:627-630; Esterbauer, H, Gebicki, J, Puhl, H, & Jürgens, G, Free Radic Biol Med 1992, 13:341-390).

Methods of measuring oxidized lipids are well known to those of skill in the art (see, e.g., Vigo-Pelfrey et al. Membrane Lipid Oxidation, Volume I-II. CRC Press). such methods include, but are not limited to mass spectrometry, absorption spectrometry (e.g., using UV absorbance at 234 nm), liquid chromatography, thin layer chromatography, and the use of various "oxidation-state" sensitive reagents, e.g. in various redox reactions.

Previously known methods for measuring oxidized lipids (e.g. lipid peroxides), include the Wheeler method, iron thiocyanate method, thiobarbituric acid method, and others. The Wheeler method (Wheeler (1932) Oil and Soap, 9: 89-97) is that in which oxidized lipid is reacted with potassium iodide to isolate iodine, which is then titrated with a sodium thiosulfate standard solution. In the iron thiocyanate method (Stine et al. (1954) J. Dairy Sci., 37: 202) oxidized lipid peroxide is mixed with ammonium thiocyanate and ferrous chloride, and the blue color from the resulting iron thiocyanate is calorimetrically determined. In the thiobarbituric acid method (Tappel and Zalkin (1959) Arch. Biochem. Biophys., 80: 326) the lipid peroxide is heated under acidic conditions and the resulting malondialdehyde is condensed with thiobarbituric acid to form a red color dye, which is then calorimetrically measured.

In another approach, it has been demonstrated that peroxidase decomposes lipid peroxides and that the resulting reaction system colors intensely with increasing quantities of lipid peroxide, if an adequate hydrogen donor is present in the reaction system (see, e.g., U.S. Pat. No. 4,367,285) Thus, in one embodiment, the assays of this invention may utilize a peroxidase and a hydrogen donor.

Many peroxidases are suitable. The peroxidase employed in the present invention is preferably any of the commercially available horseradish peroxidases.

The hydrogen donor employed may be any of the known oxidizable compounds which, preferably, generate color, fluorescence or luminescence upon oxidation. The conventional coloring, fluorescent, luminescent reagents may be utilized. The known coloring reagents which may be employed include, but are not limited to guaiacol, 4-aminoantipyrine with phenol, 4-aminoantipyrine with N,N-dimethylaniline, 3-methyl-2-benzothiazolinone with dimethylaniline, ortho-dianisidine, and the like. Typically useful fluorescent reagents include, but are not limited to homovanillic acid, p-hydroxyphenylacetic acid, and the like. Suitable luminescent reagents include but are not limited to luminol and the like. The amount of the hydrogen donor employed is preferably at least equimolar, preferably not less than two moles, per mole of lipid peroxide contained in test sample. The amount may be varied depending upon the size of the sample and the content of the lipid peroxide in the sample.

Suitable reaction mediums which may be employed include, but are not limited to dimethylglutarate-sodium hydroxide buffer solution, phosphate buffer solution and, Tris-hydrochloric acid buffer solution is normally from about pH 5 to about pH 9.

Such factors as the pH at the time of reaction, the reaction period, the measuring wavelength, etc., may be varied depending upon the reagents employed. Suitable conditions can be selected according to the circumstances.

Another class of assays for oxidized lipids is described in U.S. Pat. No. 4,900,680. In this approach, an oxidized lipid (e.g. a hydroperoxide) is reacted with a salt or hydroxide of a transition metal which produces a cation having a valency of 2, a complex of a transition metal having a valency of 2, a heme, a heme peptide, a heme protein, or a heme enzyme. The resultant active oxygen and oxygen radicals react with a luminescent substance, and light emitted by this reaction is optically measured. Examples of a catalyst acting on a lipid hydroperoxide to produce active oxygen species such as active oxygen or oxygen radicals are: a transition metal salt which produces a cation having a valency of 2 (e.g., ferrous chloride, ferrous sulfate, potassium ferricyanide, each of which produces $Fe^{2+}$; manganous chloride or manganous sulfate, each of which produces $Mn^{2+}$; or cobalt chloride or cobalt sulfate, each of which produces $Co^{2+}$); a hydroxide of the transition metals described above; a complex of a transition metal having a valency of 2 (e.g., FeII-porphyrin complex); a heme protein (e.g., cytochrome C, hemoglobin, or myoglobin); a heme peptide (e.g., a compound obtained by decomposing a heme protein by a protease such as chymotrypsin or trypsin); and a heme enzyme (e.g., horseradish peroxidase or prostaglandin peroxidase).

Particular catalyst compounds include, but are not limited to, a heme protein, a heme peptide, or a heme enzyme. Most usually, the heme protein such as cytochrome C is used due to easy handling. The concentration of the catalyst compound preferably ranges from about 0.1 µg/ml to about 1,000 µg/ml and usually falls within the range of about 1 µg/ml to about 200 µg/ml. For example, best luminous efficiency can be obtained when the concentration is about 10 µg/ml for cytochrome C, about 120 µg/ml for cytochrome C heme peptide; and about 10 µg/ml for horseradish peroxidase.

The luminescent substance is not limited to a specific one, provided it reacts with active oxygen or an oxygen radical to emit light. Examples of such a compound include, but are not limited to polyhydroxyphenols (e.g., pyrogallol, perprogalline etc.), phthaladine derivatives (e.g., luminol, isoluminol, etc.), indol derivatives (e.g., indoleacetic acid, skatole, tryptophan, etc.); thiazolidine derivatives (e.g., Cyprindinacea luciferin, lophine, etc.), an acrydine derivatives (e.g., lucigenine), oxalic acid derivatives (e.g., bistrichlorophenyloxalate); and 1,2-dioxa-4,5-azine derivatives. The concentration of the luminescent substance varies depending on the compound used. The concentration is preferably 0.1 μg/ml or more. When luminol is used, its concentration is most preferably 1 μg/ml.

Measurements are preferably performed in a weak basic solution of a luminescent reagent such as a heme protein and luminol. A particular pH value ranges from about pH 9 to about pH 10. Many buffers are suitable. One particular buffer is a borate buffer ($H_3BO_3$—KOH), a carbonate buffer ($Na_2CO_3$—$NaHCO_3$), a glycine buffer ($NH_2CH_2COOH$—NaOH), or the like. The borate buffer is most preferred.

In order to prevent oxygen dissolved in the luminescent reagent solution from interfering with the analysis of a very small amount of oxidized lipid, the luminescent reagent solution is desirably purged with an inert gas to remove oxygen to obtain a stable measurement value. Examples of the inert gas are nitrogen gas and argon gas.

The concentration of the oxidized lipid in the sample is calculated based on a calibration curve. The calibration curve can be formed according to standard methods, e.g., by using a material selected from methyl linolate hydroperoxide, arachidonic acid hydroperoxide, phosphatidylcholine hydroperoxide, phosphatidylethanolamine hydroperoxide, and triacylglycerol hydroperoxide.

The methods of this invention may utilize fluorescent materials whose fluorescence is altered by oxidation state. Such fluorescent materials are well known to those of skill in the art and include, but are not limited to 2'7'-dichlorodihydrofluorescine diacetate, rhodamine cis-parinaric acid, NBD, cis-parinimic acid cholesteryl esters, diphenylhexatriene proprionic acid, and the like. The use of such indicators is illustrated in the examples.

It will be appreciated that the foregoing methods of detecting/quantifying oxidized lipids are intended to be illustrative and not limiting. Numerous other methods of assaying oxidized lipids are known to those of skill in the art and are within the purview of this application.

The TBA test has been challenged because of its lack of specificity, sensitivity, and reproducibility. The use of liquid chromatography instead spectrophotometer techniques help reduce these errors. In addition, the test seems to work best when applied to membrane systems such as microsomes. Gases such as pentane and ethane are also created as lipid peroxidation occurs. These gases are expired and commonly measured during free radical research. Dillard (Dillard et al. Free Radic Biol Med. 1989; 7(2):193-6) was one of the first to determine that expired pentane increased as VO2 max increased. Kanter et al. (Kanter M M, Nolte L A, Holloszy J O, J Appl Physiol. 1993 February; 74(2):965-9) has reported that serum MDA levels correlated closely with blood levels of creatine kinase, an indicator of muscle damage. Lastly, conjugated dienes (CD) are often measured as indicators of free radical production. Oxidation of unsaturated fatty acids results in the formation of CD. The CD formed are measured and provide a marker of the early stages of lipid peroxidation (Poirier B, Michel O, Bazin R, Bariety J, Chevalier J, Myara I. Nephrol Dial Transplant. 2001 August; 16(8): 1598-606). A newly developed technique for measuring free radical production shows promise in producing more valid results. The technique uses monoclonal antibodies and may prove to be the most accurate measurement of free radicals. However, until further more reliable techniques are established it is generally accepted that two or more assays be utilized whenever possible to enhance validity.

When glutathione or glutathione peroxidase (which uses selenium) or ADP for regeneration of oxidized glutathione is deficient, blood lipid peroxide and subsequently urine lipid peroxide would increase.

Oral ingestion of IMMUNE FORMULATION 100™ or IMMUNE FORMULATION 200™ can replenish glutathione levels and have a vital antioxidant effect, thus, reducing blood lipid peroxide and consequently urine lipid peroxide.

This metabolite, urine lipid peroxide, can mirror the body's antioxidant need and mirror the utilization efficiency of IMMUNE FORMULATION 100™ or IMMUNE FORMULATION 200™ to remediate that deficiency. It can also mirror the effectiveness of glutathione synthesis from IMMUNE FORMULATION 100 or IMMUNE FORMULATION 200™ during that deficiency. However, the amount of IMMUNE FORMULATION 100™ or IMMUNE FORMULATION 200™ needed to reverse the deficiency is to be quantified so as to establish a cause and effect interrelationship.

The following equation demonstrates that a toxic peroxide can be detoxified by glutathione to form water and oxidized G-S-S-G.

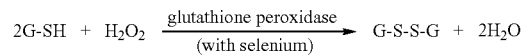

The high level of toxic lipid peroxide in the urine would indicate that sufficient glutathione or selenium is not available to detoxify that peroxide. This can be tested and proven by quantifying the collaboration between the oral ingestion of specified amounts of IMMUNE FORMULATION 100™ or IMMUNE FORMULATION 200™ and the reduction of lipid peroxide in the urine. Concurrent measurement of plasma glutathione levels would be made to confirm that the therapy resulted in synthesis or resynthesis of glutathione levels. The normal range for glutathione in the plasma is about 200-400 mole/L (AmScot™, Cincinnati, Ohio).

Therefore, oral ingestion of an antioxidant such as IMMUNE FORMULATION 100™ or IMMUNE FORMULATION 200™ should result in reduced urinary excretion of lipid peroxide and increased levels of glutathione synthesis in blood plasma, thus proving that these three functions are interrelated and interdependent.

There are several methods and kits available and known to those skilled in the art for measuring the presence of lipid peroxide in bodily fluids, including urine. Using these methods, the normal range of urine lipid peroxide is about 8.9 to 13.3 nM/mg creatinine (Metametrix Clinical Laboratory, Norcross, Ga.). Using this as the normal range, the physician assessing his or her patient for the level of oxidative stress can use one of the validated means for measuring urine lipid peroxide and obtain a value for that patient to determine where he or she is in relation to this normal value. If the level increases to a level outside of the normal range, he or she is in need of therapy with an anti-oxidant. In one particular embodiment, a patient in need of anti-oxidant therapy has a urine level of lipid peroxide which is above the normal range. Preferably, the anti-oxidant of choice is IMMUNE FORMULATION 100™ or 200™, although other anti-oxidant therapies are also contemplated for use with the invention.

Furthermore, upon initiation of therapy with an anti-oxidant, it is of use to determine the utilization efficiency of such therapy by monitoring changes in urine lipid peroxide, to determine if the level is being adjusted to within the normal range. In addition, these levels would be monitored throughout the course of therapy to determine the effectiveness of therapy with the anti-oxidant. The measurement of urine lipid peroxide may be done prior to, concurrently with, or shortly thereafter, a measure of urine pyroglutamic acid and plasma glutathione levels in order to provide a secondary confirmation and assessment of the patient's oxidative stress level. Furthermore, these tests may be combined with other test parameters to determine whether the patient has recovered sufficiently in order for therapy with the anti-oxidant to be discontinued. For example, in the case of a patient suffering from diabetes or high cholesterol or high triglyceride levels, the physician may assess other parameters such as glycated hemoglobin, glucose levels or request a full battery of blood chemistries to assess the overall health status of the individual before discontinuing therapy with the anti-oxidant.

The methods for measuring lipid peroxidation products and lipid peroxidation damage in tissues, cells and body fluids have been described above. The choice of which method is most appropriate depends, among other things, on whether the measurement is needed for strictly research purposes, or for a particular medical situation or condition wherein the patient is under the care of a qualified physician, or health care worker, or uses a self-administered urine kit. In the routine clinical research laboratory, the determination of thiobarbituric acid reactive substances (TBARS) under strictly standardized conditions is in most cases the first choice. The specificity of the calorimetric or fluorimetric assay can be significantly improved if it is combined with analysis by HPLC methods. If the level of TBARS is increased, other more sophisticated assays should be performed for verification or validation of the values obtained. Several such assays are available including: Phospholipid- and cholesterylester hydroperoxides, aldehydic lipid peroxidation products including 4-hydroxynonenal, fluorescent protein adducts (e.g. lipofuscin), conjugated dienes and antioxidants. The measurement of pentane and ethane in the exhaled air by gas chromatography has been the only available non-invasive method, although this assay method has its own drawbacks in that it is time consuming and cumbersome to run routinely. Several laboratories have also developed immunological assays such as the enzyme-linked immunosorbent assay (ELISA) or the radioimmunoassay (RIA) for determining proteins modified by lipid peroxidation products (e.g. malondialdehyde, 4-hydroxynonenal) or autoantibodies against oxidatively modified proteins. These assays provide a much more convenient and quantitative assessment of the by-products of oxidation and are much less cumbersome and time consuming to run as compared to the HPLC or other standard chemical approaches for assay and quantitation.

Under standard laboratory practice, and for assessment of a patient's clinical condition, an increased concentration of end products of lipid peroxidation is the evidence most frequently cited for the involvement of free radicals in human disease. However, while it is recognized that the generation of free radicals and the subsequent oxidative damage resulting from their presence occurs in most diseases, it is also true that oxidative damage plays a significant pathological role in only some of these diseases. This is true, for example, in atherosclerosis and in exacerbation of the initial tissue injury caused by ischemic or traumatic brain injury or spinal cord injury, where peroxidation of the surrounding cells and tissues appears to be extremely important in the pathology of these conditions. Moreover, it is also becoming more apparent that stress plays a role in reduction in immune responsiveness to known pathogens and that this may be due in part to reduced levels of glutathione. (Leonore A. Herzenberg et al, Proc. Natl. Acad. Sci. USA Vol. 94, pp. 1967-1972, March 1997) Oxidative stress can damage many biological molecules including proteins, DNA and lipids. Many assays are available to measure lipid peroxidation, but no single assay is an accurate measure of the whole process. Application of simple diene-conjugate and thiobarbituric acid (TBA) assays to human tissues and body fluids can produce artifacts. Thus, it is important to utilize other methods for assessment of a more accurate clinical profile.

Some of the methods used to monitor oxidative products include the following:

Determination of Urinary Thiobarbituric-Acid-Reacting Substances (TBARS)

This procedure involves the incubation of a sample of urine with 5% butylated hydroxytoluene (in glacial acetic acid) and 0.5% aqueous thiobarbituris acid (TBA) solution (Buege J A, Aust S D: Microsomal lipid peroxidation. *Methods Enzymol* (1978), 52:302-310; Valenzuela A: The biological significance of malondialdehyde determination in the assessment of tissue oxidative stress. *Life Sci* 1991, 48:301-309). After mixing and incubating the mixture for about 30 minutes, the absorbance is measured at 532 nm using a spectrophotometer. The quantity of TBARS is proportional to the amount of malondialdehyde (MDA), a lipid peroxidation product generated by the oxidation of lipids by reactive oxygen species. MDA reacts with TBA to form a 1:2 MDA:TBA adduct that absorbs at 532 nm. To control for urine concentration, data are normalized to urine creatinine concentrations as described by Coulthard et al. (Coulthard M G, Hey E N, Ruddock V: Creatinine and urea clearances compared to inulin clearance in preterm and mature babies. *Early Hum Dev* 1985, 11:11-19).

Measurement of 8-epi-prostaglandin PGF2a (8-epi-PGF2a)

The appearance of 8-epi-prostaglandin PGF2a (8-epi-PGF2a) in plasma or urine has been suggested by a number of investigators as a reliable index of in vivo free radical generation and oxidative lipid formation. There is very strong evidence from animal studies that 8-epi-PGF2a increase in plasma and urine as a result of oxidative stress, and in human, this product is elevated in smokers. Comparison with other measures of lipid peroxidation, 8-epi-PGF2a is specific product of lipid peroxidation, and is very stable. In addition, its formation is modulated by antioxidant status, and its level is not affected by lipid content of the diet. The measurement of 8-epi-prostaglandin PGF2 can be done using a standard immunoassay using antibodies specific for this by-product of lipid oxidation.

ELISA kits for measurement of 8-hydroxy-2'-deoxyguanosine (8-OHdG)

8-OhdG is a nucleotide which is excised from DNA. Endonuclease repair enzymes work quickly therefore the amount excised in urine directly reflects a person's degree of damage in the body. These kits, which are available from Genox, measure the amount of 8-hydroxy-2'-deoxyguanosine (8-OHdG) in urine, serum, plasma, tissue homogenate and digested lymphocyte DNA samples. Genox is a distributor of products developed by the Japan Institute for the Control of Aging. Furthermore, Genox also sells a monoclonal antibody against 8-OhdG for immunohistochemical studies on tissue samples. These kits contain the following.

---

8-OHdG coated microtiter plate (split type)
Primary antibody (Anti-8-OHdG monoclonal antibody)
Primary antibody solution -continued Secondary antibody (POD-conjugated anti mouse antibody)
Secondary antibody solution
Chromatic solution (3,3',5,5'-tetramethylbenzidine)
Substrate solution
Washing solution
Reaction terminating solution
Standard 8-OHdG solution (0.5, 2, 8, 20, 80, 200 ng/ml)
Plate seal The general procedure is as follows:
(1) Primary Antibody Reaction (Competitive Reaction): 37° C. for 1 hour
(2) Secondary Antibody Reaction: 37° C. for 1 hour
(3) Development of Color Reaction: Room Temperature for 15 min in the dark
(4) Absorbance Reading (wavelength at 450 nm) and Calculation of Results Additional methods for measuring 8-hydroxy-2'-deoxyguanosine (8-OHdG) are essentially as outlined in the following references, which are incorporated in their entirety. (S. S. Kantha, S. Wada, H. Tanaka, M. Takeuchi, S. Watabe, and H. Ochi Carnosine sustains the retention of cell morphology in continuous fibroblast culture subjected to nutritional insult. *Biochemical and Biophysical Research Communications,* 223, 278-282 (1996); S. S. Kantha, S. Wada, M. Takeuchi, S. Watabe, and H. Ochi, A sensitive method to screen for hydroxyl radical scavenging activity in natural food extracts using competitive inhibition ELISA for 8-hydroxydeoxyguanosine; *Biotechnology Techniques,* 10(12), 933-936 (1996); J. Leinonen, T. Lehtimaki, S. Toyokuni, K. Okada, T. Tanaka, H. Hiai, H. Ochi, P. Laippala, V. Rantalaiho, O. Wirta, A. Pasternack, and H. Alho, New biomarker evidence of oxidative DNA damage in patients with non-insulin-dependent diabetes mellitus; *FEBS Letters,* 417, 150-152 (1997); H. Tsuboi, K. Kouda, H. Takeuchi, M. Takigawa, Y. Masamoto, M. Takeuchi, and H. Ochi, 8-Hydroxydeoxyguanosine in urine as an index of oxidative damage to DNA in the evaluation of atopic dermatitis, *British Journal of Dermatology,* 138, 1033-1035 (1998); Y. Miyake, K. Yamamoto, N. Tsujihara, and T. Osawa Protective effects of lemon flavonoids on oxidative stress in diabetic rats. *Lipids,* 33(7), 689-695 (1998); M-H. Kang, M. Naito, N. Tsujihara, and T. Osawa Sesamolin inhibits lipid peroxidation in rat liver and kidney. *Journal of Nutrition,* 128, 1018-1022 (1998); T. Arimoto, T. Yoshikawa, H. Takano, M. Kohno Generation of reactive oxygen species and 8-hydroxy-2'-deoxyguanosine formation from diesel exhaust particles components in L1210 cells. *Japanese Journal of Pharmacology,* 80, 49-54 (1999); M. D. Evans, M. S. Cooke, I. D. Podmore, Q. Zheng, K. E. Herbert, and J. Lunec, Discrepancies in the measurement of UVC-induced 8-oxo-2'-deoxyguanosine: Implications for the analysis of oxidative DNA damage. *Biochemical and Biophysical Research Communications,* 259, 374-378 (1999)).

AntiOxidant Check by Body Balance is a safe, easy-to-use, and reliable test that uses a small urine sample to measure free radical activity by measuring lipid peroxide levels. The kit provides a sample collection device for urine, which is collected and forwarded to a laboratory for analysis.

Oxis Bioxytech LPO586 from Oxis International (Seattle, Wash.) is a calorimetric assay for evaluating lipid peroxidation. The results are specific for malondialdehyde and 4-hydroxyalkenals, which are markers of lipid peroxidation.

Methods for Measuring Glutathione

Glutathione is recycled and reutilized in the kidney, after its three constituent amino acids are broken down in the renal tubules. Any amino acid that is not considered healthy or optimal is theoretically excreted via the renal tubules, and glutathione cannot be resynthesized unless it gains an optimal amount of its three precursor amino acids, cysteine, glycine and glutamate. When there is a deficiency of one of these amino acids, especially cysteine, glutathione cannot optimally be resynthesized. It is thus broken down and excreted in the urine via its constituent parts as waste products, one of which is pyroglutamic acid, described below. PGA is a crucial marker of glutathione breakdown and its deficient reutilization in the kidney. Therefore, it is crucial to establish the level of this depletion and to determine whether IMMUNE FORMULATION 100™ or IMMUNE FORMULATION 200™ can replenish glutathione levels and reverse the excessive excretion of urine lipid peroxide. It would be possible to use urine PGA as a marker of glutathione need, glutathione utilization, and glutathione resynthesis and of IMMUNE FORMULATION 100™ or IMMUNE FORMULATION 200™ efficiency. Thus, high urine PGA is a marker for glutathione need, diminished glutathione utilization and deficient glutathione resynthesis.

Several methods are currently available for measuring glutathione levels. The normal level of plasma glutathione as measured by AmScot™ in Cincinnati, Ohio is about 200-400 mole/L. The methods for measurement of glutathione are listed below.

The Bioxytech GSH-400 kit from Oxis International (Seattle, Wash.) is a non-enzymatic, calorimetric assay specific for glutathione.

Cayman Chemical produces a glutathione assay kit, which utilizes a carefully optimized enzymatic recycling method, using glutathione reductase for the quantification of GSH. (Baker, M. A., Cerniglia, G. J., and Zaman, A. Microtiter plate assay for the measurement of glutathione (GSH) and glutathione disulfide (GSSG) in large numbers of biological samples. Anal. Biochem. 190, 360-365 (1990); Eyer, P. and Podhradsky, D. Evaluation of the micromethod for determination of glutathione using enzymatic cycling and Ellman's reagent. Anal. Biochem. 153, 57-66 (1986); Tietze, F. Enzymic method for quantitative determination of nanogram amounts of total and oxidized glutathione: Applications to mammalian blood and other tissues. Anal. Biochem. 27, 502-522 (1969)). Briefly, the sulfhydryl group of GSH reacts with DTNB (5,5'-dithio-bis-2-nitrobenzoic acid, Ellman's reagent) and produces a yellow colored 5-thio-2-nitrobenzoic acid (TNB). The mixed disulfide, GSTNB (between GSH and TNB) that is concomitantly produced, is reduced by glutathione reductase to recycle the GSH and produce more TNB. The rate of TNB production is directly proportional to this recycling reaction, which in turn is directly proportional to the concentration of GSH in the sample. Measurement of the absorbance of TNB at 405 or 412 nm provides an accurate estimation of GSH in the sample. GSH is easily oxidized to the disulfide dimer GSSG. Because of the use of glutathione reductase in the Cayman GSH assay kit, both GSH and GSSG are measured and the assay reflects total glutathione. The kit can also be used to measure only GSSG by following an alternative protocol. GSH measurement can be done in plasma, tissue samples, and cultured cells using this kit. Nearly all samples require deproteination before assay.

Methods for Measuring Pyroglutamic Acid

The presence of pyroglutamic acid (PGA), also known as 5-oxoproline, in the urine is an indication of a defect in the γ-glutamyl cycle, a series of enzyme-linked reactions involved in the synthesis, metabolism, and transcellular transport of glutathione. Furthermore, it is present in urine in patients suffering from diseases or conditions which induce high levels of oxidative stress, such as those conditions outlined in the present application. In these conditions, the presence of abnormally high levels of PGA is an indication that glutathione levels are low and that there is a defect in glutathione re-synthesis. The normal laboratory range for PGA is <80 µg/mg of creatinine (MetaMetrix Clinical Laboratory, Norcross, Ga.). The levels of creatinine are measured using standard clinical laboratory procedures known to those skilled in the art.

One object of the present invention is to determine if and how much IMMUNE FORMULATION 100™ or 200™ would diminish PGA excretion in the urine and how much IMMUNE FORMULATION 100™ or 200™ would be needed to increase glutathione synthesis or resynthesis during this deficiency. Glutathione levels would be tested in blood plasma while PGA would be tested concurrently in the urine. Most preferably, both urine lipid peroxides and PGA would both be measured concurrently with plasma glutathione to aid in accuracy of the test results and to establish a more precise assessment of the need for treatment with an antioxidant, such as IMMUNE FORMULATION 100™ or 200™. Therefore, oral ingestion of an antioxidant such as IMMUNE FORMULATION 100™ or IMMUNE FORMULATION 200™ should result in reduced urinary excretion of PGA and increased levels of glutathione synthesis in blood plasma, thus proving that these three functions are interrelated and interdependent.

Thus, analysis of a urine sample for measurement of PGA from a patient experiencing oxidative stress can be done using standard gas chromatography-mass spectrometry techniques and would demonstrate a markedly increased excretion of 5-oxoproline or PGA in a patient experiencing oxidative stress and would correlate with lowered plasma glutathione levels.

PGA measurements can be done by gas chromatography using a Hewlett-Packard 5890 series II fitted with 7673A autosampler, HP-1 capillary column (25 m×0.2 mm×0.33-µm film thickness; Hewlett-Packard), and HP5971A mass-selective detector. Helium gas flow rate can be 0.6 mL/min (head pressure, 114 kPa). Split injections (ratio, 100:1) can be made with a 1-µL sample. A one-step temperature program may be run from 70 to 290° C. at 7° C./min after an initial time of 0.5 min. The mass spectrometer in electron ionization mode, connected directly to the capillary column outlet, would be operated at 70 eV. Data aquisition can be carried out in the scan mode from m/z 58 to 550, with dwell time of 100 ms. The method of extraction and preparation of urine samples for gas chromatography-mass spectrometry and the method for qualitatively and quantitatively identifying 5-oxoproline are based on those described by Tanaka et al. (Tanaka K, West-Dull A, Hine D G, Lynn T B, Lowe T. Gas chromatographic method of analysis for urinary organic acids. I. Retention indices of 155 metabolically important compounds. Clin Chem 1980; 26:1839-1846; Tanaka K, West-Dull A, Hine D G, Lynn T B, Lowe T. Gas chromatographic method of analysis for urinary organic acids. II. Description of the procedure and its application to diagnosis of patients with organic acidurias. Clin Chem 1980; 26: 1847-1853). The response factor to the internal standard, isopentanoic acid, could be used to approximate the 5-oxoproline peak as identified by comparison with published spectra.

Amino acid measurements, including measurement of glutathione in urine, plasma, and whole-blood hemolysate could be made with a Biotronic LC5001 amino acid analyzer (Eppendorf-Netheler-Hinz, division of Biotronics) and a Trivector TR10 computing integrator (Trivector Technical Services). A glass separation column (3.2×385 mm) could be used with BTC2710 10-µm separation exchangeresin (Eppendorf-Netheler-Hinz) and lithium citrate separation buffer (flow rate, 0.30 mL/min). Separation temperatures would be set at 32° C. for 44 min, 34° C. for 28 min, and 60° C. for 31 min. For colorimetric peak detection at 570 and 440 nm, 500 µmol/L aminoethyl-L-cysteine hydrochloride in 37 mmol/L lithium/76 mmol/L citrate buffer at pH 2.2 would be used as the internal standard. Plasma, urine, and whole-blood hemolysate would be pretreated with crystalline 5-sulfosalicylic acid as a deproteinization step.

Treatment Groups

As noted above, it is generally recognized that many disease processes are attributed to the presence of elevated levels of free radicals and reactive oxygen species (ROS) and reactive nitrogen species (RNS), such as superoxide, hydrogen peroxide, singlet oxygen, peroxynitrite, hydroxyl radicals, hypochlorous acid (and other hypohalous acids) and nitric oxide. Furthermore, subjects suffering from any of these conditions may benefit from therapy with anti-oxidants. It is with respect to these particular diseases and conditions that the current invention would be beneficial, particularly with respect to assessing the need of the patient for treatment with anti-oxidant therapy and for monitoring the effectiveness of such therapy. Moreover, the novel IMMUNE FORMULATIONs described in U.S. Pat. Nos. 6,667,063 and 6,592,908 would be beneficial for treatment of these patients and the amount and duration of therapy with these novel compositions, as well as other anti-oxidant formulations may be monitored effectively using the methods of the present invention. A summary of particular diseases for which anti-oxidant therapy would be beneficial and for which monitoring the need for and effectiveness of such therapy using the methods described herein follows.

The methods of the present invention may be utilized to assess an individual's need for specific therapy with an antioxidant, and as such, may be considered as a means to assess either an individual's current medical condition and needs, or alternatively, the methods may be used as a prophylactic means to allow identification of individuals of particularly high risk for diseases known to be associated with high oxidative stress, such as, but not limited to, atherosclerosis and cardiovascular disease. Upon such identification, such subjects can adopt more frequent testing, dietary adjustments, monitoring and regulation of blood pressure, and the like. As a diagnostic assay, the methods of this invention supplement traditional testing methods to identify subjects known to be at risk who may prove resistant to conventional therapeutic regimens and alter the prescribed treatment. Thus, for example, where a subject is diagnosed with early stages of atherosclerosis, a positive test using the assays of this invention may indicate additional drug intervention rather than simply dietary or lifestyle changes.

Cardiovascular Disease

Oxidative modification of low density lipoproteins (LDL) is recognized as one of the major processes involved in atherogenesis and cardiovascular disease. Thus, a measurement of LDL oxidative susceptibility could be of clinical significance (Scoccia A E et al, BMC Clin Pathol. (2001) 1(1):1). Furthermore, more precise measurements of both lipid oxidation and pyroglutamic acid measurements in the urine, as well as plasma glutathione measurements as outlined in the present invention could be even more beneficial in terms of assessing the patients' need for treatment with both an anti-oxidant as well as lipid lowering drugs and would also be beneficial in terms of monitoring the utilization efficiency of these drugs as well as the effectiveness of therapy.

Cancer

The role of oxidative stress in many cancers has been under investigation for many years. However, it is recently becoming more apparent that reactive oxygen or nitrogen species may in fact affect signaling pathways in many hyperproliferative disorders. For example, prostate cancer (PC) has become the most frequently diagnosed neoplasm and the second leading cause of cancer-related mortality in men. Its incidence rate has continued to increase rapidly during the past two decades, especially in men over the age of 50 years as they are living longer. The prostate in aging males is highly susceptible to benign and malignant proliferative changes. It is believed that about two/thirds of all cancers could have been prevented based upon lifestyle choices. How environment, diet and genetics interact to either induce or prevent prostate cancer (PC) is not known. Free radicals play a significant but paradoxical role acting as a "double-edged sword" to regulate cellular processes. That is, because of their effect on cell signaling pathways and in particular, apoptosis, it appears that ROS may prevent apoptosis and can thus maintain proliferation in certain cancer cells. Thus, there appears in certain instances to be a paradoxical role for ROS in these situations. Recent in vitro studies using benign prostate hyperplasia (BPH) and PC cell lines grown under various oxidative stress conditions confirm this theory. Key signal transduction mechanisms may be involved in ROS induced effects on prostate cell growth, cell-cycle checkpoints, apoptosis and transcription factors. Thus, dietary antioxidants may have a beneficial effect on these mechanisms (Sikka S C Curr Med Chem (2003) 10(24):2679-92).

Furthermore, it is also known that many of the therapies available for treatment of cancers are associated with oxidative tissue damage. For example, adriamycin is known to induce cardiac and hepatic toxicity. Studies have been done with specific agents to determine their effects on such peroxidative damage induced by adriamycin (ADR). For example, a study was conducted to determine the effect of a heparin derivative, low molecular weight heparin (LMWH) on the biochemical changes, tissue peroxidative damage and abnormal antioxidant levels in adriamycin (ADR) induced cardiac and hepatic toxicity (Deepa P R et al, Chem Biol Interact (2003) 146(2):201-10). LMWH administration to ADR-induced rats prevented the rise in serum and tissue levels of LDH, aminotransferases and ALP, while these parameters were significantly elevated in the ADR group in comparison with the control group. Cardiotoxicity indicated by rise in serum CPK in the ADR group was attenuated by LMWH treatment in group IV. LMWH decreased the cardiac and hepatic lipid peroxidation induced by ADR. Histologic examination revealed that the ADR-induced deleterious changes in the heart and liver tissues were offset by LMWH treatment. Restoration of cellular normalcy accredits LMWH with cytoprotective role in adriamycin-induced cardiac and hepatic toxicity.

Carboplatin is currently being used as an anticancer drug against human cancers. However, high dose of carboplatin chemotherapy result in ototoxicity in cancer patients. Carboplatin-induced ototoxicity is related to oxidative stress to the cochlea and inner hair cell loss in animals. It is likely that initial oxidative injury spreads throughout the neuroaxis of the auditory system later. A study was done to evaluate carboplatin-induced hearing loss and oxidative injury to the central auditory system (inferior colliculus) of the rat (Husain, K. et al. Int J. Toxicol. (2003) 22(5):335-42). Carboplatin significantly increased nitric oxide and lipid peroxidation, xanthine oxidase, and manganese superoxide dismutase activities in the inferior colliculus, but not in the cerebellum, indicating an enhanced flux of free radicals in the central auditory system. Carboplatin significantly depressed the reduced to oxidized glutathione ratio, antioxidant enzyme activities, such as copper-zinc superoxide dismutase, catalase, glutathione peroxidase, glutathione reductase, and glutathione S-transferase, and enzyme protein expressions in the inferior colliculus, but not in the cerebellum, 4 days after treatment. The data suggest that carboplatin induced oxidative injury specifically in the inferior colliculus of the rat leading to hearing loss.

Neurological Diseases and Conditions

Oxidative stress, which is now recognized as accountable for redox dysregulation involving reactive oxygen species (ROS) and reactive nitrogen species (RNS) plays a pivotal role for the modulation of critical cellular functions, notably for cells in the neuronal system (Emerit J, Edeas M, Bricaire F. Biomed Pharmacother. 2004 January; 58(1):39-46; Smith J V et al, J. Alzheimer's Dis. (2003) 5(4):287-300; Hayashi T. et al, J Cereb Blood Flow Metab (2003) 23(10):1117-28; Niu K C et al. Clin. Exp. Pharmacol. Physiol. (2003) 30(10):745-51), in particular, neurons, astrocytes and microglia, such as apoptosis program activation, and ion transport, calcium mobilization, involved in excitotoxicity. Excitotoxicity and apoptosis are the two main causes of neuronal death. The role of mitochondria in apoptosis is crucial. Multiple apoptotic pathways emanate from the mitochondria. The respiratory chain of mitochondria (oxidative phosphorylation), is the fount of cellular energy, i.e. ATP synthesis, and is responsible for most of ROS and notably the first produced, superoxide anion. Mitochondrial dysfunction (i.e. cell energy impairment, apoptosis and overproduction of ROS), is a final common pathogenic mechanism in aging and in neurodegenerative disease such as Alzheimer's disease (AD), Parkinson's disease (PD) and amyotrophic lateral sclerosis (ALS). Nitric oxide (NO), an RNS, which can be produced by three isoforms of NO-synthase in brain, plays a prominent role.

The etiology of neurodegenerative diseases remains enigmatic; however, evidence for defects in energy metabolism, excitotoxicity, and for oxidative damage is increasingly compelling. There is most likely a complex interplay between these mechanisms. A defect in energy metabolism may lead to neuronal depolarization, activation of N-methyl-D-aspartate excitatory amino acid receptors, and increases in intracellular calcium, which are buffered by mitochondria. Mitochondria are the major intracellular source of free radicals, and increased mitochondrial calcium concentrations enhance free radical generation. Mitochondrial DNA is particularly susceptible to oxidative stress, and there is evidence of age-dependent damage and deterioration of respiratory enzyme activities with normal aging. This may contribute to the delayed onset and age dependence of neurodegenerative diseases. There is evidence for increased oxidative damage to macromolecules in amyotrophic lateral sclerosis, Huntington's disease, Parkinson's disease, and Alzheimer's disease. Potential therapeutic approaches include glutamate release inhibitors, excitatory amino acid antagonists, strategies to improve mitochondrial function, free radical scavengers, and trophic factors. All of these approaches appear promising in experimental studies and are now being applied to human studies. (Beal M F, Ann Neurol. 1995 September; 38(3):357-66)

The role of amyloid beta-peptide (Abeta) in the free-radical oxidative-stress model of neurotoxicity in Alzheimer's disease (AD) has received much attention recently. Studies have been done to study the effects of Abeta on intracellular free radical levels. A neuroblastoma cell line, which stably expresses an AD-associated double mutation, which exhibits both increased secretion and intracellular accumulation of Abeta when stimulated was utilized in one study. In addition, a transgenic *Caenorhabditis elegans* constitutively expressing human Abeta was also used. A rise in levels of hydrogen peroxide (H2O2) was observed in both in vitro and in vivo AD-associated transgenic models expressing the Abeta peptide compared with the wild type controls. Furthermore, an age-dependent increase in H2O2-related ROS was observed in wild type *C. elegans*, which is accelerated in the AD-associated *C. elegans* mutant. These results support the hypothesis of the involvement of Abeta and ROS in association with AD (Smith, J. V. and Luo, Y. (2003), J. Alzheimers Dis. 5(4):287-3000).

The endoplasmic reticulum (ER), which plays important roles in apoptosis, is susceptible to oxidative stress. Because reactive oxygen species (ROS) are robustly produced in the ischemic brain, ER damage by ROS may be implicated in ischemic neuronal cell death. A study was done whereby global brain ischemia was induced in wild-type and copper/zinc superoxide dismutase (SOD1) transgenic rats and ER stress and neuronal damage was compared. Phosphorylated forms of eukaryotic initiation factor 2 alpha (eIF2 alpha) and RNA-dependent protein kinase-like ER eIF2 alpha kinase (PERK), both of which play active roles in apoptosis, were increased in hippocampal CA1 neurons after ischemia but to a lesser degree in the transgenic animals. This finding, together with the finding that the transgenic animals showed decreased neuronal degeneration, indicates that oxidative ER damage is involved in ischemic neuronal cell death (Hayashi T. et al. (2003), J. Cereb. Blood Flow Metab. 23(10): 1117-1128).

Inflammatory Diseases

The role of oxidative stress in inflammatory diseases has also been investigated. For example, Ramos et al. determined the level of cellular oxidative stress blood markers and the enzymatic system of antioxidant defense in patients suffering from juvenile rheumatoid arthritis (JRA) (Ramos V A et al., (2000), J Pediatr (Rio J), 76(2): 125-32). This study included 64 patients. The patients were separated in three subtypes based on the pattern of onset within the first six months of disease: polyarticular, pauciarticular and systemic. The control group included 60 patients (38 of female sex) following clinical control to diseases of non inflammatory nature, in the same hospital. The plasmatic levels of malondialdehyde (MDA), lipoperoxide (LPO), hydroperoxide (HPX), carbonile groups (CG) of proteins and gluthathione and the enzymatic activities of Superoxide dismutase (SOD), gluthathione peroxidase (GSH-Px) and gluthathione reductase were determined. The results showed that the group of patients with JRA presented high concentrations of lipid peroxidation products, evaluated by determining the plasmatic levels of MDA, LPO, and HPX; oxidative damage of the circulate protein, determined by CG contents of plasma proteins; elevation of enzymatic activity of SOD and GSH-Red; decrease of GSH-Px activity and GSH levels. These results demonstrated the presence of molecular damage that generated oxygen free radicals in the JRA patients. The SOD activity and the changes of gluthathione redox enzymatic cycle confirm the decrease of capacity of cellular defense system against the induced toxicity of oxidative stress in these patients Drug Induced Oxidation The generation of free radicals in vivo can be attributed to many things. For example, many known drugs can increase the production of free radicals in the presence of increased oxygen tensions. These drugs may include antibiotics that depend on quinoid groups or bound metals for activity (nitrofurantoin), antineoplastic agents as bleomycin, anthracyclines (adriamycin, see above) (Fisher, 1988) and methotrexate, which possess pro-oxidant activity (Gressier et al. 1994). In addition radicals derived from penicillamine, phenylbutazone, some fenamic acids and the aminosalicylate component of sulphasalazine might inactivate protease and deplete ascorbic acid accelerating lipid peroxidation (Grisham et al. 1992; Halliwel et al. 1992a; Evans et al. 1994).

Radiation Therapy Induced

Radiotherapy may cause tissue injury as a result of free radical generation. Electromagnetic radiation, such as X rays or gamma rays, and particulate radiation, such as electrons, photons, neutrons, alpha and beta particles, may generate primary radicals by transferring their energy to cellular components including water. These primary radicals can undergo secondary reactions with dissolved oxygen or with cellular solutes.

Smoking Induced

The presence of oxidants in tobacco may play a major role in injuring the respiratory tract. For example, the oxidants in tobacco smoke severely deplete intracellular antioxidants in lung cells in vivo. The mechanism for doing so is related to oxidant stress. The oxidant materials that are present for a time sufficient to cause damage to the alveoli include aldehydes, epoxides, peroxides, and other free radicals. In addition, nitric oxide, peroxyl radicals and carbon centered radicals are present in the gas phase, while other radicals are present in the tar phase. Examples of radicals in the tar phase include the semiquinone moieties derived from various quinones and hydroquinones. Micro-haemorrhages are most probably the cause of iron deposition found in smokers' lung tissue. This form of iron may lead to the formation of the lethal hydroxyl radical from hydrogen peroxide. Furthermore, smokers have elevated amounts of neutrophils in the lower respiratory tract. These may contribute to a further elevation of the concentration of free radicals.

Providing a Biological Sample for Use in the Methods of the Present Invention

In particular embodiments the assays are performed using a biological sample from the organism/subject of interest. While the assays are of great use in humans, they are not so limited. It is believed similar oxidative damage exists essentially in all mammals and thus the assays of this invention are contemplated for veterinary applications as well. Thus, suitable subjects include, but are not limited to humans, non-human primates, canines, equines, felines, porcines, ungulates, lagomorphs, and the like.

A suitable biological sample includes a sample of a biological material, which may be selected from a blood sample or urine. As used herein a blood sample includes a sample of whole blood or a blood fraction (e.g. serum or plasma). The sample may be fresh blood or stored blood (e.g. in a blood bank) or blood fractions. The sample may be a blood sample expressly obtained for the assays of this invention or a blood sample obtained for another purpose, which can be subsampled for the assays of this invention. In a preferred embodiment, the bodily sample is preferably plasma or urine.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions, employing one of a variety of buffers, such as phosphate, Tris, or the like, at physiological pH can be used.

Lipid and Water-Soluble Antioxidants

As described below, there are many known lipid and water soluble antioxidants known to have beneficial effects in treatment of various disease conditions, whereby high levels of oxidative stress may be responsible in part for progression of the tissue damage associated with such diseases and conditions. It would be beneficial to utilize the methods of the present invention to monitor utilization efficiency and effectiveness of these therapies should it be determined that a patient would benefit from such therapies. While these antioxidants are believed to be useful in the treatment of the diseases and conditions described herein, it is believed that therapy with glutathione precursors, IMMUNE FORMULATION 100™ or IMMUNE FORMULATION 200™ would be the most preferred embodiments.

Lipid Soluble Anti-Oxidants

Lutein: A very active lipid-soluble carotenoid antioxidant (2.3 times higher than vitamin E), which is readily absorbed into the serum. Lutein and zeaxanthin are major factors in the prevention of macular degeneration, which is, the leading cause of blindness in the elderly and represents 10% of all blindness in humans.

Zeaxanthin: A very active lipid-soluble carotenoid antioxidant (2.8 times higher than vitamin E) which is readily absorbed into the serum. Lutein and zeaxanthin are implicated in the prevention of macular degeneration, which is the leading cause of blindness in the elderly and represents 10% of all blindness in humans.

Beta-Cryptoxanthin:—Probably the most active of the lipid soluble antioxidants (3.1 times higher than vitamin E) which is readily absorbed into the serum.

Lycopene: One of the most active lipid-soluble antioxidants (2.8 times higher than vitamin E). Research has indicated that lycopene may be very important in the prevention of prostate cancer.

Alpha-Carotene: A known antioxidant and precursor to vitamin A. Experimental evidence shows that alpha carotene is a stronger antioxidant and cellular differentiating agent than beta carotene and therefore may be better in preventing cancer.

Beta Carotene: A known antioxidant and precursor to vitamin A, which has been most widely researched and used extensively as a diet supplement. It is a strong cellular differentiating agent, and therefore may prevent cancer.

Retinol [Vitamin A]: A known antioxidant and cellular differentiating agent and Therefore may prevent cancer and many aspects of aging.

Retinyl Palmitate: The retinol ester that is most commonly used in dietary Supplements and foods as a source of vitamin A.

Carotenoid classes: This grouping of carotenoids contain many uncharacterized carotenoids that most likely are beneficial to health. This value provides a good overall value of the amounts of fruits and vegetables being consumed.

Alpha-Tocopherol (Vitamin E):—One of the best characterized and diet supplemented lipid-soluble antioxidants. Apart from its antioxidant capabilities, it has cellular differentiation properties which are believed to be good in preventing cancer.

Delta-Tocopherol (Vitamin E): Not much is known about the beneficial effects of delta-tocopherol to humans, though it is normally found at lower amounts in foods and human serum.

Gamma-Tocopherol (Vitamin E): The major type of vitamin E found in the heart and therefore may be selected for the body because of its unique properties either as an antioxidant or as a differentiation agent.

Ubiquinol [Coenzyme Q10]: Is normally synthesized in cells as part of the mitochondrial oxidative phosphorylation system and is present in lipid biomembranes. COQ10 can also be absorbed through the diet and can act as a very active antioxidant and protecting LDL from becoming oxidized.

Water-Soluble Antioxidants

Vitamin C [Ascorbate] (in serum and saliva) Ascorbic acid can directly scavenge oxidative species as well as generate other oxidized antioxidants such as vitamin E. However, under conditions where there are free prooxidant metals around, such as iron and copper, vitamin C's strong reductive capacity will catalyze the production of oxidative free radicals.

Thiols (in serum and saliva) are very active antioxidants and reducing agents. Most serum thiols are found in albumin as indicated by free cysteine and glutathione. Albumin thiols are thought to act as sacrificial antioxidants that have little biological consequences of being damaged. Because of their high antioxidant reactivity and high concentration, albumin thiols act as a major defense against free radical damage to cell membranes.

Uric acid (in serum and saliva) Uric acid is a methylxanthine (like caffeine) which stimulates brain activity. It is also known to directly scavenge oxidative species and chelate prooxidant metals.

Direct and Total Bilirubin: This is considered as a waste product of heme metabolism. Bilirubin is known to be a very active lipid and aqueous soluble serum antioxidant. Direct (conjugated) bilirubin is the form of bilirubin that can be absorbed and removed from the body in the bile.

IMMUNE FORMULATION 100™ and IMMUNE FORMULATION 200™

The methods described herein contemplate the use of several anti-oxidant therapies effective at treating various diseases or conditions in which oxidative stress plays a role. However, a preferred embodiment provides for the use of IMMUNE FORMULATION 100™ or IMMUNE FORMULATION 200™ for administration to subjects experiencing oxidative stress or immune dysfunction. These formulations were developed for use as a nutritional supplement that is beneficial if taken on a daily basis. These formulations have the benefit of supplying the glutathione precursors needed for resynthesis of glutathione when the levels are depleted due to disease or metabolic dysfunction. In addition, they are safe and cost effective for those patients in need of daily consumption. Furthermore, they can be formulated as chewable tablets or as nutritive bars or wafers. In another embodiment, it is envisioned that IMMUNE FORMULATION 100% or IMMUNE FORMULATION 200™ can be used in combination with any of the anti-oxidants discussed above of the present invention.

IMMUNE FORMULATION 100™

The essential components in IMMUNE FORMULATION 100™ are a selected whey product, colostrum and a non-toxic catalytic quantity of elemental selenium or a water soluble precursor of elemental selenium in an amount sufficient to aid in the production of glutathione. Selenium precursors are much preferred since they are easier to handle.

Selenium is one of numerous trace metals found in many foods. Selenium may be employed as one of several non-toxic, water soluble, organic or inorganic selenium compounds capable of being absorbed by the body. The presently preferred inorganic selenium compounds are aliphatic metal salts containing selenium in the form of selenite or selenate anions. However, organic selenium compounds are more preferred because they are normally less toxic than inorganic compounds. Other selenium compounds which may be mentioned by way of examples include selenium cystine, selenium methionine mono- and di-seleno carboxylic acids with about seven to eleven carbon atoms in the chain. Seleno amino acid chelates are also useful. Selenium compounds are utilized in this composition in amounts to provide selected quantities of elemental selenium.

A second component of IMMUNE FORMULATION 100™ is whey. Whey is the curd-free portion of milk that remains after the production of cheese. "Whey" is a term referring to the serum or watery part of milk after removal of the cheese. Removal of a substantial portion of the water results in a dry whey. There are two common types of dry whey. These are dry whey concentrates and dry whey isolates. The former (WPC) is an off-white to cream colored product which, depending on the method of manufacture, may contain from about 15% to 85% protein based on the total weight. It may additionally contain small amounts of minerals, vitamins and carbohydrates. Whey protein isolate (WPI) contains more than 85% by weight of protein. Both types of whey are available from Proliant, Manhattan, Ill.; Davisco Foods International, Inc. Eden Prairie, Minn. or Land-O-Lakes, Tulare, Calif. The whey product may be up to about 35% denatured. The whey product may be completely denatured, but the cost of wholly denatured whey is such that it is not feasible to employ wholly undenatured whey in compositions to serve general human consumption or in animal needs. Accordingly, the dried whey product utilized in IMMUNE FORMULATION 100™ will be a whey product concentrate or whey product isolate which is up to about 35% denatured or, conversely about 65% to about 100% undenatured. Preferably, it will contain from about 65% to about 85% protein. It may comprise from about 5% to about 95% of the composition based on the total weight of the composition.

A third component of IMMUNE FORMULATION 100™ is colostrum. Colostrum is a thin milky fluid secreted by the mammary gland of mammals a few days before or after parturition. It is a unique combination of beneficial nutrients including protective antibodies, fat, carbohydrate, vitamins and minerals. The immunological components of colostrum include IgG, IgM and IgA. These components confer passive immunity to the neonate and protection against infection during the initial period after parturition. After this period, colostrum is no longer absorbed through the gut and the newborn must depend upon its own developing immune system for protection. Colostrum is an important factor in the growth of mammals including humans, bovines, caprines, porcines and equines. The preferred colostrums for use in the compositions of this invention are bovine and caprine. Several colostrum products useful in this formulation are commercially available.

The daily effective dosage of the products of this invention will depend upon the size of the individual (human or animal) being treated, the condition being treated, the age of the individual and other factors well known to the physician or veterinarian in attendance. The optimum daily dosage can easily be determined by a few simple observations. It will generally vary from about 250 mg to 2000 mg per day for humans and small animals. For large animals the daily dosage will normally be from about 500 mg to 5000 mg per day. While these are projected dose ranges, the methods of the present invention can be utilized to measure utilization efficacy and ultimate effectiveness of these formulations.

IMMUNE FORMULATION 200™

The essential components of IMMUNE FORMULATION 200™ are precursors of glutathione, namely glutamic acid, cystine or another cysteine precursor and glycine, together with a catalytic quantity of a selenium source. The separate components serve as precursors with selenium for the metabolic formation of glutathione after they have been transported across the mucous membrane. The glutathione precursors in this formulation, which are a mixture of glutamic acid, cystine or another related cystine precursor, and glycine are in a molar ratio of about 1:0.5:1, the amount of glutathione precursors being effective to increase the content of glutathione in the body tissue of the mammal above that of a pretreatment level thereby to enhance immune activity. This material is further described and claimed in U.S. Pat. No. 6,592,908. The composition may be used alone, but normally it will be employed in association with one or more non-toxic pharmaceutically acceptable carriers appropriate to the method of administration. If an excess of any amino acid is used, it will presumably be of nutritional value or may simply be metabolized.

IMMUNE FORMULATION 200™ will be utilized to increase the formation of glutathione and thus to enhance the immune activity of a mammal in need of such treatment. The effect of the treatment is such that after the treatment, the mammal will be more resistant to microbial infection or other trauma, diseases, or conditions adversely affecting immune activity than before such treatment.

Because of its ability to increase production of glutathione, IMMUNE FORMULATION 200™ is useful to treat a wide variety of diseases or conditions associated with the presence of excess free radical or reactive oxygen or nitrogen species. These include, for example, cancer, Alzheimer's disease, arteriosclerosis, rheumatoid arthritis and other autoimmune diseases, cachexia, coronary artery disease, chronic fatigue syndrome, AIDS and others as described herein.

The components of this composition are amphoteric and therefore may be employed as non-toxic metal salts or acid addition salts. Typically, the salts are alkalic or alkaline earth metal salts, preferably sodium, potassium or calcium salts. Suitable acid addition salts include salts of hydrochloric, phosphoric and citric acid. The amino acids may also be employed in the form of certain of their derivatives including esters and anhydrides which before or after transport through the mucous membrane will be modified into the form in which they will be joined together to form glutathione. All amino acids employed, except glycine which does not form optical isomers, are in the natural or L-form. Although wide variations are possible, it will be apparent that the optimum ratio of glutamic acid to cystine to glycine in this novel composition described herein is 1:0.5:1. If an excess of any acid is used, it will presumably be of nutritional value or may simply be metabolized.

It is important for the use of this composition that the selenium as employed in the composition be capable of transport through the mucosal membrane of the patient under treatment. For this reason, water insoluble selenium compounds are not generally useful.

For convenience, the term "selenium" is sometimes used hereinafter to include any of the various water soluble selenium products which can be transported through the mucosal membrane in the practice of this invention. It will be understood, however, that the particular forms of selenium compounds set forth herein are not to be considered limitative. Other selenium compounds, which exhibit the desired activity and are compatible with the other components in the mixture and are non-toxic, can be used in the practice of the invention. Many of them are available commercially.

In fact, the amount of selenium precursor employed in this novel composition is only enough to provide a catalytic quantity of the element to activate the glutathione system. The catalytic quantity of selenium precursor utilized in the compositions of this invention is such that it will produce either in one dosage unit or in multiple dosage units sufficient elemental selenium to promote the production and activation of glutathione.

Typically, this will be at or near the recommended daily allowance of selenium for the individual mammal under treatment. This amount will be well below the toxicity limit for elemental selenium. By way of non-limiting examples, a representative range of catalytic quantities of selenium precursors is based on the age of the individual. The recommended daily allowances for elemental selenium as reported in The Pharmacological Basis of Therapeutics, Ninth Edition, page 1540, The McGraw-Hill Companies, 1996. The recommended daily dosage for humans therefore ranges from 10 to 75 μg per day. For animals the range may depend upon the animal and its size.

The tablets or wafers, with fillers will typically weigh from about 0.5 to 5 grams and will contain a therapeutically effective amount of the essential ingredients together with the selected vehicle. Tablets and other forms of the immunoenhancing compositions can be prepared to provide any quantity of elemental selenium from less than 1 μg to 7.5 μg. For example, a tablet containing 10 μg of selenium methionine is capable of delivering 4 μg of elemental selenium, and 7.5 μg of selenium methionine is capable of delivering 3 μg of selenium. Tablets may be given several times per day to achieve the desired immune enhancing effect.

A one a day tablet weighing two grams may contain 200 mg or more of the composition. A similar tablet intended to be used every four hours may contain 50 mg to 100 mg or more of the therapeutically effective composition.

Immune Function Analysis

The methods of the present invention provide for measurement of specific immune cell numbers and activities, including quantitation of specific T cell subsets and function of natural killer cells. In particular, CD4+ T cells and CD8+ T cells provide immune protection from all forms of pathogens, including bacteria, viruses, and tumors. These cells act as a source of cytokines/lymphokines for induction of cytolytic T cells, one of the primary immune cells that lyse virus infected target cells as well as tumor targets. These cells also secrete factors that aid in the induction of specific B cell or antibody producing cell populations.

Assays for measuring the numbers of these cell populations are known to those skilled in the art. For example, as shown below, the most commonly used procedures are by FACS analysis, whereby the cell populations are incubated with labeled antibodies specific for cell surface markers. These antibodies may be labeled with phycoerythrin or FITC and after a period of time, they are washed and analyzed in a fluorescent activated cell sorter. Alternatively, assays can be set up to measure the activity of these cells in a specific chromium release assay to assess their activity. These assays are also known to one skilled in the art.

Natural killer (NK) cells are one of the early defense mechanisms in the body for protection against a variety of pathogens. These cells may also be assessed by the use of specific cell surface markers and FACS analysis. Alternatively, their activity may be assessed using NK sensitive target cells in a chromium release assay as described below.

Assay Formats

The methods of this invention may use assays which may be practiced in almost a limitless variety of formats depending on the particular needs at hand. Such formats include, but are not limited to traditional "wet chemistry" (e.g. as might be performed in a research laboratory), high-throughput assay formats (e.g. as might be performed in a pathology or other clinical laboratory), and "test strip" formats, (e.g. as might be performed at home or in a doctor's office).

Traditional Wet Chemistry

The assays of this invention can be performed using traditional "wet chemistry" approaches. Basically this involves performing the assays as they would be performed in a research laboratory. Typically the assays are run in a fluid phase (e.g. in a buffer with appropriate reagents (e.g. lipids, oxidized lipids, oxidizing agent, etc.) added to the reaction mixture as necessary. The oxidized lipid concentrations are assayed using standard procedures and instruments, e.g. as described in the examples.

High-Throughput Assay Formats

Where population studies are being performed, and/or in clinical/commercial laboratories where tens, hundreds or even thousands of samples are being processed (sometimes in a single day) it is often preferably to perform the assays using high-throughput formats. High throughput assay modalities are highly instrumented assays that minimize human intervention in sample processing, running of the assay, acquiring assay data, and (often) analyzing results. In particular embodiments, high throughput systems are designed as continuous "flow-through" systems, and/or as highly parallel systems.

Flow through systems typically provide a continuous fluid path with various reagents/operations localized at different locations along the path. Thus, for example a blood sample may be applied to a sample receiving area where it is mixed with a buffer, the path may then lead to a cell sorter that removes large particulate matter (e.g. cells), the resulting fluid may then flow past various reagents (e.g. where the reagents are added at "input stations" or are simply affixed to the wall of the channel through which the fluid flows. Thus, for example, the sample may be sequentially combined with a lipid (e.g. provided as an LDL), then an oxidation agent, an agent for detecting oxidation, and a detector where a signal (e.g. a calorimetric or fluorescent signal) is read providing a measurement of oxidized lipid.

In highly parallel high throughput systems samples are typically processed in microtiter plate formats (e.g. 96 well plates, 1536 well plates, etc.) with computer-controlled robotics regulating sample processing reagent handling and data acquisition. In such assays, the various reagents may all be provided in solution. Alternatively some or all of the reagents (e.g. oxidized lipids, indicators, oxidizing agents, etc.) may be provided affixed to the walls of the microtiter plates.

In a particular embodiment of the present invention, it is envisioned that all three products, that is, lipid peroxides, pyroglutamic acid and glutathione may be measured concurrently. For example, a 96 well plate may be prepared that contains wells to which antibodies have been attached for each of the three products. Thus, one set of thirty two wells would contain an antibody to lipid peroxides, one set of wells would contain an antibody to glutathione, and a third set of thirty two wells would contain an antibody prepared to pyroglutamic acid. Thus, urine samples can be applied to the wells containing the antibodies to lipid peroxides and to those wells containing antibodies to pyroglutamic acid. Whole blood or blood plasma can be added to those wells containing antibodies to glutathione. After an appropriate incubation time, for example, 1 hour at 37° C., the plates would be washed, and secondary antibodies which are conjugated to (labeled with) an enzyme or fluorophore can be added, incubated in the same manner, and the amount of secondary label bound can be measured using a substrate for the enzyme or if the fluorophore method is used, the amount of label bound is measured using spectrophotometric techniques at the appropriate wavelength for the fluorophore.

High throughput screening systems that can be readily adapted to the assays of this invention are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols. Thus, for example, Zymark Corp. provides technical bulletins describing screening systems for detecting the modulation of gene transcription, ligand binding, and the like.

"Test Strip" Assay Formats

The methods of the present invention may also utilize assays which are provided in "test well" or "test strip" formats. In "test well" or "test strip" formats, the biological sample is typically placed in the well or applied to a receiving zone on the strip and then a fluorescent or calorimetric indicator appears which, in this case, provides a measure of the protection or repair afforded by the subject's HDL or components thereof.

Many patents have been issued which describe the various physical arrangements for blood testing. These include systems which involve lateral or horizontal movement of the blood, as well as plasma testing. For example, U.S. Pat. Nos. 4,876,067, 4,861,712, 4,839,297, and 4,786,603 describe test carriers and methods for analytical determination of components of bodily fluids, including separating plasma from blood using glass fibers and the like. These patents, all teach systems which require some type of rotation of test pads or a portion of the test pads during use. U.S. Pat. No. 4,816,224 describes a device for separating plasma or serum from whole blood and analyzing the serum using a glass fiber layer having specific dimensions and absorption to separate out the plasma from the whole blood for subsequent reaction. Similarly, U.S. Pat. No. 4,857,453 describes a device for performing an assay using capillary action and a test strip containing sealed liquid reagents including visible indicators. U.S. Pat. No. 4,906,439 describes a diagnostic device for efficiently and accurately analyzing a sample of bodily fluid using fluid delivery in a lateral movement via flow through channels or grooves.

Kits

The methods of the present invention provide for measuring the amounts of specific markers of oxidative stress. In a particular embodiment, at least three markers are quantitated using standard reagents and kits, which are commercially available to measure each marker individually. In another particular embodiment, the methods further comprise the measurement of the number and/or activity of specific immune cell populations, preferably T cells and natural killer cells using techniques known to those skilled in the art. Thus, the present invention provides a more quantitative and accurate means of assessing a subject's need for antioxidative therapy by measuring all of these parameters concurrently. To the inventor's knowledge, no other art currently exists which describes combining the concurrent non-invasive techniques and measurements described herein for assessing the need for, and to measure the effectiveness of, therapy with antioxidants.

However, one of the oxidative markers, pyroglutamic acid, is measured using non-immunological techniques, in particular, gas chromatography and mass spectrometry are used. While this procedure provides the accuracy and sensitivity that is needed for such measurements in the present invention, the procedure can be time consuming and requires the use of very specialized equipment. Accordingly, the present invention also provides for kits comprising binding partners for the oxidative markers and the reagents needed for detection of the oxidative stress markers. The kits of the present invention provide advantages over those commercially available in that at least three oxidative markers can be measured concurrently using the same assay format. In another embodiment, the kits may contain binding partners for the three oxidative stress markers, that is, for lipid peroxide, pyroglutamic acid and glutathione, as well as binding partners for cell surface markers on CD4+ T cells, CD8+ T cells and a cell surface marker for natural killer cells, such as NK1.1/CD69. Thus, a kit of the present invention may be useful for monitoring both markers of oxidative stress as well as markers for immune cells known to be beneficial against known pathogens.

Thus, an assay format is preferred in which binding partners such as antibodies can be obtained or prepared for the analytes (lipid peroxide, pyroglutamic acid, glutathione, CD4, CD8, NK1.1/CD69). Biotin-avidin, biotin-streptavidin or other biotin-binding-reagent reactions can be used to enhance or modulate the test. However, any such assay can be devised using other binding partners to the analytes (oxidative stress markers and immune cell markers), including but not limited to extracellular or intracellular receptor proteins which recognize the analytes, binding fragments thereof, hybridization probes for nucleic acids, lectins for carbohydrates, etc. The particular selection of binding partners is not limiting, provided that the binding partners permit the test to operate as described herein. The preselected analytes, when present, are detectable by binding two binding partners, one immobilized on the test strip (or whatever format the assay is provided) and another part of a conjugate. This is taken into consideration in the selection of the reagents for the assay.

The dry test strip may be set up in any format in which contact of the sample with the reagents is permitted and the formation and mobility of the immunocomplexes and other complexes forming therein are permitted to flow and contact an immobilized reagent at the capture line. Various formats are available to achieve this purpose, which may be selected by the skilled artisan.

The label portion of the mobile, labeled antibody to the marker may be a visible label, such as gold or latex, an ultraviolet absorptive marker, fluorescent marker, radionuclide or radioisotope-containing marker, an enzymatic marker, or any other detectable label. A visibly detectable marker or one that can be easily read in a reflectometer is preferred, for use by eye, reading or confirmation with a reflectometer. Other labels may be applicable to other semi-automated or automated instrumentation.

The conjugates of the invention may be prepared by conventional methods, such as by activation of an active moiety, use of homobifunctional or heterobifunctional cross-linking reagents, carbodiimides, and others known in the art. Preparation of, for example, a gold-labeled antibody, a conjugate between an antibody and an analyte (not an immunocomplex but a covalent attachment which allows each member to independently exhibit its binding properties), biotinylation of an antibody, conjugation of streptavidin with a protein, immobilization of antibodies on membrane surfaces, etc., are all methods known to one of skill in the art.

A kit may have at least one reagent for carrying out an assay of the invention, such as a kit comprising a conjugate between a biotin-binding reagent and an antibody to an oxidative marker. Preferably, the kit comprises all of the reagents needed to carry out any one of the aforementioned assays, whether it be homogeneous, heterogeneous, comprise a single conjugate of the marker conjugated to an antibody to the analyte, or comprise two reagents which serve this function (such as a biotinylated antibody to the analyte plus a streptavidin-marker conjugate, or a biotinylated marker plus a streptavidin conjugated to an antibody to the analyte conjugate), or whether the assay employs an immobilized antibody to the analyte and a labeled antibody to a different site on the analyte. Referring to the first analyte as analyte and the second analyte as marker, and a second binding partner as a binding partner which recognizes a different epitope than the first binding partner mentioned, the following kits are non-limiting examples of those embraced herein:

In the foregoing kits, the binding partners are preferably antibodies or binding portions thereof, and both the binding partner to the analytes (the three oxidative stress markers, and the markers for immune cells) and the second binding partner to the analytes capable of simultaneously binding to the analyte. The immobilized binding partner may be provided in the form of a capture line on a test strip, or it may be in the form of a microplate well surface or plastic bead, by way of non-limiting examples. The kits may be used in a homogeneous format, wherein all reagents are added to the sample simultaneously and no washing step is required for a readout, or the kits may be used in a multi-step procedure where successive additions or steps are carried out, with the immobilized reagent added last, with an optional washing step.

The antibodies specific for the three oxidative stress markers may be obtained commercially, or can be produced by techniques known to those skilled in the art.

EXAMPLES

The following examples are put forth so as to provide those of ordinary skill in the art with a complete disclosure and description of how to use the methods described herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Assessment of the Effects of IMMUNE FORMULATION 100™ or 200™ on Adriamycin Induced Oxidative Stress Levels in Rats Adriamycin, while being an effective anti-cancer agent in humans, is known to induce nephropathy in a rat model (Zima, T. et al (1998), Nephrol. Dial. Transplant, 13: 1975-1979). Its deleterious effects on the kidney are believed to be due in part on the generation of reactive oxygen species (ROS) following its metabolism in vivo. Thus, the administration of adriamycin in a rat model provides an opportunity to study the effects of this compound on the generation of reactive oxygen species by measuring the by-products of such ROS, such as urinary lipid peroxides and pyroglutamic acid, as well as plasma glutathione. Furthermore, one can also use this model to look at the effects of this toxic compound on kidney damage, and on numbers of immune cell populations and on natural killer cell activity. In addition, this model provides an opportunity to assess the need for treatment of an animal with an anti-oxidant, as well as monitoring the utilization efficiency of such treatment, and ultimately, to monitor the effectiveness of this treatment. Accordingly, this model will be used to study the effects of IMMUNE FORMULATION 100™ or 200™ on the normalization of urinary lipid peroxides, pyroglutamic acid and on plasma glutathione. Studies will also be done to measure the effects on CD4+ and CD8+ T cell populations, as well as on natural killer cell activity.

Materials and Methods

Rats

Ninety female Sprague-Dawley rats (200-225 g) are obtained from Charles River and acclimatized for 7 days after delivery. Animals are housed in communal cages, fed a rat maintenance diet and water ad libitum. During experiments, animals are housed in individual metabolism cages designed to separate and collect feces and urine, and given powdered diet and water ad libitum. Lighting is controlled to give a regular 12 h light-12 h dark cycle; room temperature is maintained at 21±1° C. Urine samples (24 h) are collected over ice and centrifuged (2000 r.p.m., 10 min, 4° C.) to remove hair and food debris and stored (−80° C.) in aliquots for later analysis. The general condition of the animals is monitored daily and rats are weighed twice a week.

Study Design

The rats are randomized into three groups of thirty rats per group. Group I is designated the Placebo control group, Group II is designated the Adriamycin only group, and Group III is designated the Adriamycin plus IMMUNE FORMULATION 100™ or 200™ treatment group. Twenty-four hours prior to dosing, 1.0 ml of whole blood is collected from the tail vein of each rat and placed into a heparinized microcentrifuge tube. Twenty-four hour urines are also collected from each rat prior to dosing, and the urines are centrifuged to remove any food or hair and frozen at −80° C. until assayed for the metabolites lipid peroxide and pyroglutamic acid. Plasma is separated from whole blood by centrifugation (2500×g for 25 min at 4° C.) and stored at −80° C. for glutathione analysis.

On day 1, the rats in Groups II and III are given Adriamycin at 5 mg/kg i.v., while the rats in Group I are injected with I.V. saline as placebo. On day 2, the rats in Group III are given either IMMUNE FORMULATION 100™ or 200™. IMMUNE FORMULATION 100™ will be given in a dose ranging from 5 to 125 grams per day prepared in powdered rat chow. IMMUNE FORMULATION 200™ will be given in a dose ranging from 25 to 100 mg per day by oral gavage. The rats in group III are dosed daily with the IMMUNE FORMULATIONs at the doses described. On day 4 and every three days afterwards, 1.0 ml of whole blood is collected from the tail vein of each rat in the study, and 24 hour urines are also collected. The urines and blood are treated as described above, and frozen away at −80° C. for future analysis of lipid peroxides and pyroglutamic acid.

The urine samples and plasma samples are analyzed on day seven for lipid peroxide, pyroglutamic acid and glutathione, using the methods described below. If the levels of Group III remain outside of the range of the placebo group, the rats in Group III are dose adjusted in an increment of 10 gram doses for IMMUNE FORMULATION 100™ and in increments of 10 mg doses for IMMUNE FORMULATION 200™, and dosing is continued for another week. After the rats in Group III have been dosed for a total of 2 weeks, the plasma and urine levels are again assessed for glutathione, lipid peroxide and pyroglutamic acid using the methods described below. If the ranges of all three are still outside of the range of the placebo treated Group I rats, the levels of the IMMUNE FORMULATIONs are again scaled up as described above and dosing continues another week. After one month of following this testing and dosing regimen, a final 24 hour urine sample is collected and a final bleed is done prior to sacrifice of the rats by CO2 asphyxiation. Spleens are removed and single cell suspensions are prepared for use in natural killer cell assays and for staining with markers specific for CD4+ and CD8+ T cells.

Urinary Lipid Peroxide Measurement by Determination of Urinary Thiobarbituric-Acid-Reacting Substances (TBARS)

Lipid peroxide levels in urine samples are measured colorimetrically by the thiobarbituric acid reaction (TBARS) as described in the following references: Buege J A, Aust S D, *Methods Enzymol* 1978, 52:302-310 and in Valenzuela et al (Valenzuela A: *Life Sci* 1991, 48:301-309). The level of lipid peroxides in urine is expressed as equivalents of malondialdehyde (MDA). Malondialdehyde standards are freshly prepared from tetraetoxypropane and treated in the same way as the urine samples. Briefly, 200 μl of urine is combined with 10 μl of 5% butylated hydroxytoluene (in glacial acetic acid) and 300 l of a 0.5% aqueous thiobarbituric acid (TBA) solution. The samples are vortexed and are incubated at 100° C. for 30 minutes, and the absorbance at 532 nm is measured using a PerkinElmer Lamba 3B spectrophotometer (PerkinElmer, Wellesley, Mass., USA). The quantity of TBARS is proportionate to the amount of MDA, a lipid peroxidation product generated by the oxidation of membrane lipids by reactive oxygen species. MDA reacts with TBA to form a 1:2 MDA-TBA adduct that absorbs at 532 nm. To control for urine concentration, data is normalized to urine creatinine concentrations, as described (Coulthard M G, Hey E N, Ruddock V: *Early Hum Dev* 1985, 11:11-19). Creatinine can also be measured by a Sigma diagnostics kit 555-A.

Urinary Pyroglutamic Acid Measurement

Using a range of 1 and 2 dimensional 500 MHz 1H NMR spectroscopic techniques, solid phase extraction and mass spectrometry, the metabolite pyroglutamic acid (PGA), also known as 5-oxoproline (5OXP), can be measured in the urine. (Ghauri F Y, et al. (1993), Biochem Pharmacol., September 1; 46(5):953-7.) Alternatively, PGA measurements can be done by gas chromatography using a Hewlett-Packard 5890 series II fitted with 7673A autosampler, HP-1 capillary column (25 m×0.2 mm×0.33-μm film thickness; Hewlett-Packard), and HP5971A mass-selective detector. Helium gas flow rate can be 0.6 mL/min (head pressure, 114 kPa). Split injections (ratio, 100:1) can be made with a 1-μL sample. A one-step temperature program may be run from 70 to 290° C. at 7° C./min after an initial time of 0.5 min. The mass spectrometer in electron ionization mode, connected directly to the capillary column outlet, would be operated at 70 eV. Data aquisition can be carried out in the scan mode from m/z 58 to 550, with dwell time of 100 ms. The method of extraction and preparation of urine samples for gas chromatography-mass spectrometry and the method for qualitatively and quantitatively identifying 5-oxoproline are based on those described by Tanaka et al. (Tanaka K, West-Dull A, Hine D G, Lynn T B, Lowe T. Gas chromatographic method of analysis for urinary organic acids. I. Retention indices of 155 metabolically important compounds. Clin Chem 1980; 26:1839-1846; Tanaka K, West-Dull A, Hine D G, Lynn T B, Lowe T., Gas chromatographic method of analysis for urinary organic acids. II. Description of the procedure and its application to diagnosis of patients with organic acidurias. Clin Chem 1980; 26:1847-1853). The response factor to the internal standard, isopentanoic acid, could be used to approximate the 5-oxoproline peak as identified by comparison with published spectra.

Plasma Glutathione Measurement

A GSH kit can be procured from Calbiochem. Plasma samples are defrosted and serial dilutions prepared and analyzed for total GSH per the manufacturer's instructions (Calbiochem).

Natural Killer Cell Assay

NK function (i.e., activity) can be measured by $^{51}$Cr release cytotoxicity assays against a suitable target cell. An example of a suitable target cell by which to measure NK cell cytotoxic activity is YAC-1. NK cell activation can also be measured by determining an upregulation of NK1.1/CD69 on cells in various organs, including spleen, lymph node, lung and liver, by flow cytometric analysis.

Cytotoxicity Assay

A standard 4-hour $^{51}$Cr-release assay is used to quantitate cytotoxic activity present in freshly isolated spleen mononuclear cells, using YAC-1 cells as targets. Briefly, effector cells from spleen are added in decreasing concentrations to duplicate wells of a Linbro plate, to which was then added $5×10^3$ target cells that had been previously labeled for 1 hour with $^{51}$Cr. The plates are incubated at 37° C. for 4 hours, then supernatants from each well are harvested and the amount of radioactive $^{51}$Cr present is determined by automated gamma counter. For spontaneous release, only targets were added and the well was made up to the equivalent volume with medium, for maximum release 0.1 ml of 2% SDS was added to wells containing targets only. The percentage specific lysis is calculated as ((experimental release-spontaneous release)/(maximum release-spontaneous release))×100.

Flow Cytometry

Upregulation of the early activation marker, CD69, which is upregulated on activated T cells, B cells, macrophages and NK cells, can be used to assess early immune cell activation. Single cell suspensions are prepared from spleens of rats by $NH_4Cl$ lysis procedure (Sambrook, supra). Cells are analyzed using a Becton-Dickinson FACSCalibur flow cytometer (Becton Dickinson, Mountain View, Calif.), with analysis gates set by first gating on spleen lymphocytes. Between 10,000 and 30,000 gated events are analyzed for each cell type. For analysis of cell activation, 3-color flow cytometric analysis may be done, using anti-CD69 phycoerythrin (Pharmingen, San Diego, Calif.) to quantitate the number of CD69 positive cells. Cells can also be dual-labeled to evaluate T cells (anti-apTCR antibody (biotin H57.597; Pharmingen) plus antibodies to either CD4 (FITC RM4-5; Pharmingen) or CD8 (FITC 53-6.7; Pharmingen). NK cells can be dual-labeled using anti NK 1.1 (biotin PK136; Pharmingen) and anti CD3 (FITC 2C11). The percentage of double positive cells expressing CD69 can be determined for each cell type, and the mean (+/−SD) CD69+ cells plotted.

Assessment of CD4+ and CD8+ T Cell Numbers

Monoclonal antibodies (mAbs) to murine CD4, GK1.5 (ATCC TIB 207) and murine CD8, 53-6.72 (ATCC TIB 105) are purified from hybridoma culture supernatants over a recombinant protein G column (Pharmacia, Piscataway, N.J.). As a control, purified rat IgG is purchased from Calbiochem (San Diego, Calif.). Flow cytometry is performed as described above to assess the effectiveness of the treatment regimen. Standard flow cytometric techniques are used using Phycoerythrin labeled anti-rat CD4 and FITC labeled anti-rat CD8 purchased, for example, from Pharmingen (San Diego, Calif.).

Statistical Analyses

Significant differences between groups can be determined by the Tukey-Kramer HSD multiple comparisons test using JMP® statistical discovery software (SAS Institute Inc., Cary, N.C., or by an Analysis of Variance (ANOVA) with a Bonferroni P value for multiple comparisons.

Example 2

IMMUNE FORMULATION 100™ Tablet Formulation

Ingredients:

| Whey (PROLIANT ™ 8010 or 8200) | 1 gm |
| Colostrum | 1 gm |
| Selenium methionine | 5 µg |

Blend the ingredients together and pass through a 60 mesh screen and tumble until the components are thoroughly mixed. Compress using a 7/16 inch standard concave punch.

Example 3

IMMUNE FORMULATION 100™ Powder Formulation

Ingredients:

| Whey (Proliant ™ 8010 or 8200) | 75 gm |
| Colostrum | 25 mg |
| Selenium methionine | 15 µg |

Thoroughly mix the ingredients in a blender and pass through a 80 mesh screen.

This powder may be used for mixing with animal feeds, frostings, fruit spreads and beverages to be pasteurized.

Example 4

IMMUNE FORMULATION 100™ Chewable Tablet Formulation

Ingredients:

| Vitamin A USP (dry, stabilized form) | 500 USP units |
| Vitamin D (dry, stabilized form) | 400 USP units |
| Ascorbic Acid USP | 60.0 mg |
| Thiamine Hydrochloride USP | 1 mg |
| Riboflavin USP | 1.5 mg |
| Pyridoxine Hydrochloride USP | 1 mg |
| Cyanocobalamin USP | 2 µg |
| Calcium Pantothenate USP | 3 mg |
| Niacinamide USP | 10 mg |
| Mannitol USP (granular) | 236.2 mg |
| Corn Starch | 16.6 mg |
| Sodium saccharin | 1.1 mg |
| Magnesium stearate | 6.6 mg |
| Talc USP | 10 mg |
| Whey (Proliant ™ 8010) | 8 g |
| Colostrum | 500 mg |
| Selenium methionine | 7 µg |

Thoroughly mix the ingredients in a blender and compress using a 3/8 inch bevel-edge punch.

Example 5

IMMUNE FORMULATION 200™ (Tablet)

Ingredients:

| 89 mg | cystine |
| 75 mg | glycine |
| 147 mg | glutamic acid |
| 22.5 µg | polyvinylpyrolidone |
| 61.25 mg | lactose |
| 4.5 ml | alcohol SD3A-200 proof |
| 9 mg | stearic acid |
| 42.3 mg | corn starch |
| 10 µg | selenium methionine |

Blend the cystine, glycine, glutamic acid, polyvinylpyrrolidone and lactose together and pass through a 40 mesh screen. Add the alcohol slowly and knead well. Screen the wet mesh through a 4 mesh screen. Dry the granulation at 50 degrees centigrade for 10 hours. Pass the mixture of stearic acid, corn starch and selenium compound through a 60 mesh screen and tumble with the granulation until all the ingredients are well mixed. Compress using a 7/16 inch standard concave punch.

Example 6

IMMUNE FORMULATION 200™ (Tablet)

Ingredients:

| 178 mg | cystine |
| 150 mg | glycine |
| 294 mg | glutamic acid |
| 5 µg | selenium methionine |
| 126 mg | lactose |
| 78 mg | potato starch |
| 96 mg | ethyl cellulose |
| 54 mg | stearic acid |

Thoroughly mix the ingredients in a blender, dry, put through a 12 mesh screen and compress into tablet using a 13/32 inch concave punch.

What is claimed is:

1. A method for determining an orally anti-oxidative effective amount of a nutritional or therapeutic composition sufficient to diminish urine lipid peroxide and pyroglutamic acid levels and concurrently increase blood plasma glutathione levels, comprising the steps of:
    a) collecting blood plasma and urine samples prior to administration of the nutritional or therapeutic composition and daily after the start of administration for about 14 days;
    b) measuring urine levels of lipid peroxide and pyroglutamic acid;
    c) measuring blood plasma glutathione levels;
    d) determining whether a decrease in lipid peroxide and pyroglutamic acid levels correlates with an increase in glutathione levels; and wherein said correlation establishes an orally anti-oxidative effective amount of the nutritional or therapeutic composition.

2. The method of claim 1, wherein the nutritional or therapeutic composition comprises a catalytic quantity of elemental selenium or a water soluble selenium precursor from about 5% to about 95% by weight of a special whey product containing from about 65% to about 85% protein which is from about 65% to about 100% undenatured, and from about 5% to about 95% by weight of colostrum.

3. The method of claim 1, wherein the nutritional or therapeutic composition comprises catalytic quantity of a selenium source together with glutathione precursors which are a mixture of glutamic acid, cystine or another related cystine precursor, and glycine in a molar ratio of about 1:0.5:1.

* * * * *